United States Patent
Wu et al.

(10) Patent No.: US 12,274,688 B2
(45) Date of Patent: Apr. 15, 2025

(54) DRUG-LOADED MESOPOROUS SILICA NANOPARTICLE FOR PREVENTION AND TREATMENT OF BRAIN CANCERS OR BRAIN METASTASES

(71) Applicants: NANO TARGETING & THERAPY BIOPHARMA INC, Taipei (TW); SCINOPHARM TAIWAN LTD., Tainan (TW)

(72) Inventors: Cheng-Hsun Wu, Hsinchu County (TW); Si-Han Wu, Taoyuan (TW); Rong-Lin Zhang, Pingtung County (TW); Chung-Yuan Mou, Taipei (TW); Hardy Wai Hong Chan, New Taipei (TW)

(73) Assignees: NANO TARGETING & THERAPY BIOPHARMA INC., Taipei (TW); SCINOPHARM TAIWAN LTD., Tainan (TW)

( * ) Notice: Subject to any disclaimer, the term of this patent is extended or adjusted under 35 U.S.C. 154(b) by 0 days.

(21) Appl. No.: 17/965,220

(22) Filed: Oct. 13, 2022

(65) Prior Publication Data
US 2023/0255926 A1    Aug. 17, 2023

Related U.S. Application Data

(60) Provisional application No. 63/309,119, filed on Feb. 11, 2022.

(51) Int. Cl.
*A61K 31/337* (2006.01)
*A61K 9/51* (2006.01)
*A61K 31/495* (2006.01)
*A61P 35/00* (2006.01)
*A61P 35/04* (2006.01)

(52) U.S. Cl.
CPC .......... *A61K 31/337* (2013.01); *A61K 9/5115* (2013.01); *A61K 31/495* (2013.01); *A61P 35/00* (2018.01); *A61P 35/04* (2018.01)

(58) Field of Classification Search
CPC ...... A61K 31/337; A61K 9/51; A61K 31/495; A61P 35/04; A61P 35/00
See application file for complete search history.

(56) References Cited

U.S. PATENT DOCUMENTS 11,419,826 B2   8/2022   Wu et al.
2018/0050115 A1*  2/2018  Mou .................. A61K 9/51

FOREIGN PATENT DOCUMENTS

EP   3 659 585 A1   6/2020
EP   3766482 A1     1/2021

OTHER PUBLICATIONS

Chia-Hung et al (J. Biomedical Science 28:18 (2021).*
Gisbert-Garzaran et al. (Nanomaterials (Basel). 11(9):2222 (2021).*
Cohen-Gadol (2023).*
Extended European Search Report and Search Opinion in EP Application No. 22 201 319.5, dated Jun. 15, 2023, in 7 pages.
He, Qianjun, and Jianlin Shi. "Mesoporous silica nanoparticle based nano drug delivery systems: synthesis, controlled drug release and delivery, pharmacokinetics and biocompatibility." Journal of Materials Chemistry 21.16 (2011): 5845-5855.
Glantz, M. J., et al. "The role of paclitaxel in the treatment of primary and metastatic brain tumors." Seminars in Radiation Oncology. vol. 9. No. 2 Suppl 1. 1999, 27-33, Database Medline accession No. NLM10210537, Abstract only, 1 page.
EPO First Communication (Office Action) dated Feb. 19, 2025 to the EP counterpart EP 4226914 A.
Ai-Jun et al.: Efficient delivery of docetaxel for the treatment of brain tumors by cyclic RGD-tagged polymeric micelles: Molecular Medicine Reports: vol. 11, No. 4: Apr. 1, 2015: pp. 3078-3086.

* cited by examiner

*Primary Examiner* — Shirley V Gembeh
(74) *Attorney, Agent, or Firm* — LADAS & PARRY LLP

(57) ABSTRACT

The present disclosure relates to a method of preventing or treating brain cancers or brain metastases with mesoporous silica nanoparticles (MSNs) loaded with taxane-based chemotherapeutic drugs, in particular paclitaxel (PTX), cabazitaxel (CTX) or docetaxel (DTX), and the MSNs loaded with PTX, CTX or DTX.

10 Claims, 5 Drawing Sheets

| | MST (Days) | %ILS |
|---|---|---|
| Control | 24.5 | - |
| DTX (5 mg/kg) | 20.0 | -18.4 |
| DTX (10mg/kg) | 23.0 | -6.1 |
| DTX@MSN (5 mg/kg) | 37.5 | 53.1 |
| DTX@MSN (10 mg/kg) | 45.0 | 83.7 |

MST: Median survival time
%ILS = percentage of increase in life span

DRUG-LOADED MESOPOROUS SILICA NANOPARTICLE FOR PREVENTION AND TREATMENT OF BRAIN CANCERS OR BRAIN METASTASES

CROSS-REFERENCE TO RELATED APPLICATION

This application is related to, and claims the benefit of, U.S. Provisional Application 63/309,119 filed Feb. 11, 2022, the contents of which are hereby incorporated by reference in their entirety.

FIELD OF THE INVENTION

The present invention relates to a method of preventing or treating brain cancers or brain metastases with mesoporous silica nanoparticles (MSNs) loaded with taxane-based chemotherapeutic drugs, e.g., paclitaxel (PTX), cabazitaxel (CTX) or docetaxel (DTX), and also relates to the MSNs loaded with a taxane-based chemotherapeutic drug(s), e.g., PTX, CTX or DTX, and applications thereof.

BACKGROUND OF THE INVENTION

Cancer is the leading cause of death worldwide, accounting for nearly 10 million deaths in 2020, according to WHO's records. Though various cancers can cause death and the incidence of brain cancer is not the highest, it may be the most troublesome. The human brain dominates many aspects of life, and many chemicals, including drugs, cannot penetrate the blood-brain barrier (BBB), in particular, the blood-brain-tumor barrier (BBTB) when focusing on treatment of tumors, and thus are unable to provide therapeutic functions.

Scientists and physicians have made great efforts in seeking potential drugs for treating brain cancer. Examples include temozolomide (TMZ), belzutifan, carmustine, everolimus, and lomustine, which are believed to be able to penetrate the BBB, in particular BBTB, and arrive at the site of a brain tumor. TMZ has been the first-line chemotherapeutic drug for glioma treatment for over a decade. However, TMZ may be contraindicated in certain patients, or be less effective in patients with drug resistance to TMZ. Hence, there is still a need for developing new therapeutic strategies for treating brain cancers.

Another issue is metastatic brain cancers, which might result in more death than primary brain cancers. There is a high mortality rate for patients with brain metastases. A number of commonly occurring cancers such as lung cancers, breast cancers, colon cancers, prostate cancers, etc., are especially prone to metastasize into the brain rendering. Surgery and radiation may be adopted as limited options for patients/physicians once the primary cancers have metastasized into the brain, but neither of these are especially effective. Besides surgery and radiation, TMZ still may be the only drug so far for treating metastatic brain cancers.

Using a drug delivery system may be a more efficient, effective and straight forward way to deliver drugs to a subject. For the treatment of brain cancers or brain metastasis, vesicles (lipidic, micellar, polymeric or exosomes), linear polymers, metals (Au, Gd, graphene), carbon dots, nano-implants, dendrimers, etc., may be applied as drug delivery systems. For example, mesoporous silica nanoparticles (MSNs) are deemed to have great potential as drug delivery systems due to their unique physical/chemical properties, such as large pore volume, chemical/thermal stability, high loading capacity, adjustable surface properties and excellent biocompatibility. Nevertheless, there seems to be no existing drug delivery system useful in treating brain cancers, and thus there is still a need for developing drug delivery systems, e.g., optimized MSNs, loaded with potential drugs for treating brain cancers.

SUMMARY OF THE INVENTION

The present disclosure relates to a method of preventing or treating a brain cancer or brain metastasis in a subject, comprising intravenously administering a mesoporous silica nanoparticle loaded with taxane-based chemotherapeutic drugs, e.g., paclitaxel (PTX), cabazitaxel (CTX) or docetaxel (DTX), to the subject. In particular, the mesoporous silica nanoparticle has at least one of the following characteristics:
  (a) surface modification with (i) an organic molecule, oligomer or polymer and (ii) a positively charged molecule, oligomer or polymer, wherein the molar ratio of (i) and (ii) ranges from 60:1 to 4:1;
  (b) pore surface modification with a terminal hydrocarbyl moiety;
  (c) average particle size of 60 nm or less, measured by TEM;
  (d) average dynamic light scattering particle size of 60 nm or less, measured in phosphate buffered saline (PBS) by dynamic light scattering; and
  (e) surface modification with (i) an organic molecule, oligomer or polymer.

The present disclosure also relates to a mesoporous silica nanoparticle loaded with cabazitaxel (CTX), wherein the mesoporous silica nanoparticle has at least one of the following characteristics:
  (a) surface modification with (i) an organic molecule, oligomer or polymer and (ii) a positively charged molecule, oligomer or polymer, wherein the molar ratio of (i) and (ii) ranges from 60:1 to 4:1;
  (b) pore surface modification with a terminal hydrocarbyl moiety;
  (c) average particle size of 60 nm or less, measured by TEM;
  (d) average dynamic light scattering particle size of 60 nm or less, measured in phosphate buffered saline (PBS) by dynamic light scattering; and
  (e) surface modification with (i) an organic molecule, oligomer or polymer.

The present disclosure also relates to a mesoporous silica nanoparticle loaded with docetaxel (DTX), wherein the mesoporous silica nanoparticle has at least one of the following characteristics:
  (a) surface modification with (i) an organic molecule, oligomer or polymer and (ii) a positively charged molecule, oligomer or polymer, wherein the molar ratio of (i) and (ii) ranges from 60:1 to 4:1;
  (b) pore surface modification with a terminal hydrocarbyl moiety;
  (c) average particle size of 60 nm or less, measured by TEM;
  (d) average dynamic light scattering particle size of 60 nm or less, measured in phosphate buffered saline (PBS) by dynamic light scattering; and
  (e) surface modification with (i) an organic molecule, oligomer or polymer.

The present disclosure also relates to a mesoporous silica nanoparticle loaded with paclitaxel (PTX), wherein the mesoporous silica nanoparticle has at least one of the following characteristics:
(a) surface modification with (i) an organic molecule, oligomer or polymer and (ii) a positively charged molecule, oligomer or polymer, wherein the molar ratio of (i) and (ii) ranges from 60:1 to 4:1;
(b) pore surface modification with a terminal hydrocarbyl moiety;
(c) an average particle size of 60 nm or less, measured by TEM;
(d) an average dynamic light scattering particle size of 60 nm or less, measured in phosphate buffered saline (PBS) by dynamic light scattering; and
(e) surface modification with (i) an organic molecule, oligomer or polymer.

BRIEF DESCRIPTIONS OF THE DRAWINGS

DETAILED DESCRIPTION OF THE INVENTION

Figure 1:
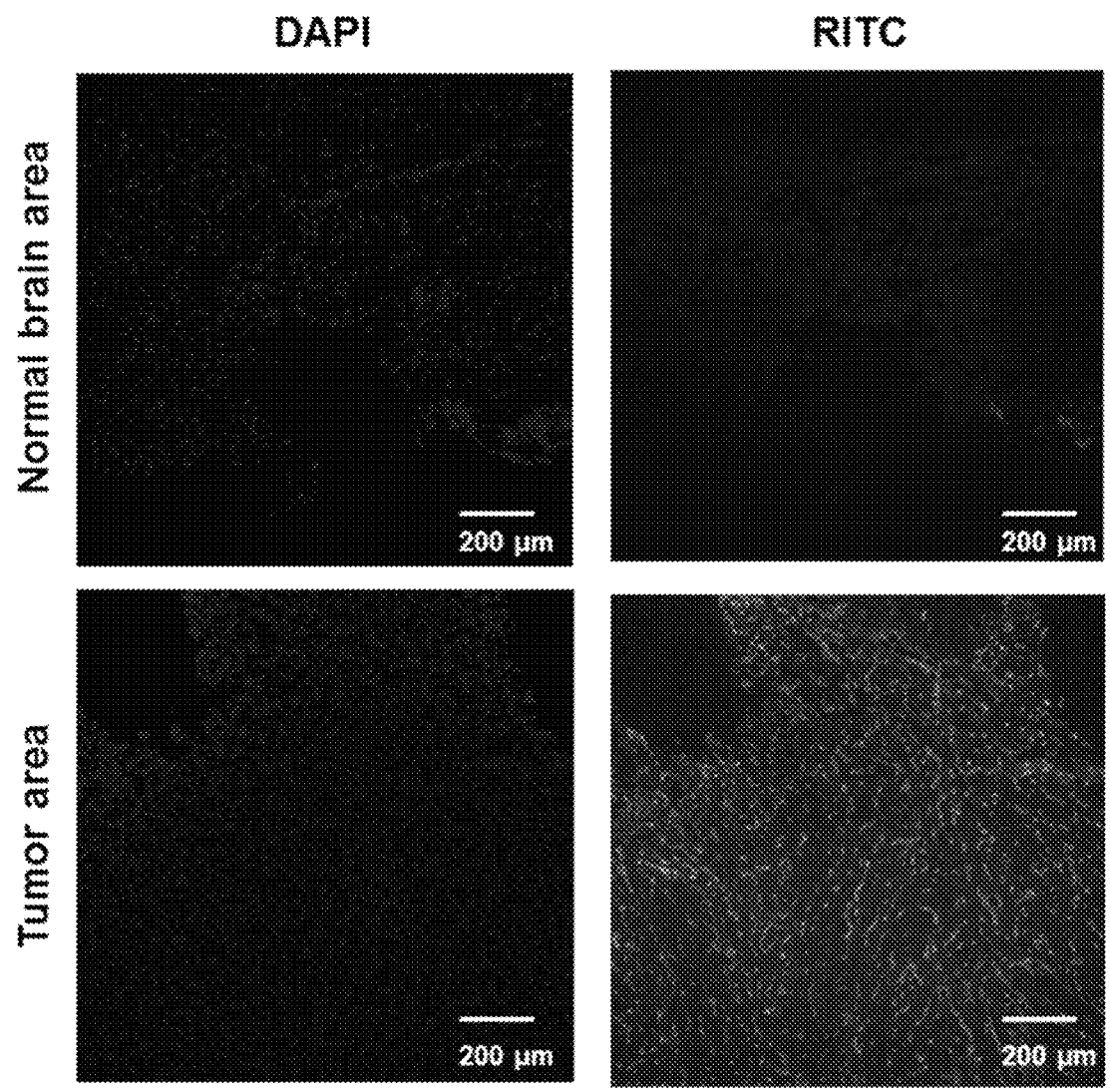
FIG. 1 shows fluorescence staining images of normal brain area and brain tumor area of one of the mice injected with fluorescence-labeled MSN.

In order to facilitate understanding of the disclosure, terms as used herein are defined below.

In the context of the specification and the claims, the singular forms, such as "a," "an" and "the," include plural referents, and vice versa, unless specifically indicated otherwise. Unless otherwise stated, any and all examples or exemplary language (e.g., "such as") provided herein is merely used for better illustration of the present invention, instead of limiting the scope of the present invention.

It is to be understood that any numerical range recited in this specification is intended to include all sub-ranges encompassed therein. For example, a range from "50 to 70° C." includes all sub-ranges and specific values between the stated minimum value of 50° C. and the stated maximum value of 70° C., inclusive, e.g., from 58° C. to 67° C., and from 53° C. to 62° C., 60° C. or 68° C. Since the numerical ranges disclosed are continuous, they contain each numerical value between the minimum and maximum value. Unless otherwise specified, the various numerical ranges indicated in this specification are approximate.

In the present invention, the term "about" refers to an acceptable deviation of a given value measured by a person of ordinary skill in the art, depending, in part, on how to measure or determine the value.

In the present invention, unless particularly specified, the prefix "nano" as used herein means a size of about 300 nm or less. Unless particularly specified, the prefix "meso" as used herein, unlike the definition suggested by IUPAC, means a size of about 50 nm or less. In certain embodiments, the prefix "meso" may refer to a smaller size of about, e.g., 20 nm or less, 10 nm or less or 5 nm or less.

In the present invention, the term "silane" as used herein refers to derivatives of $SiH_4$. Normally, at least one of the four hydrogens is replaced with substituents such as alkyl, alkoxyl, amino, etc., as described below. The term "alkoxysilane" as used herein refers to a silane having at least one alkoxyl substituent directly bonded to the silicon atom. The term "organo-alkoxysilane" as used herein refers to a silane having at least one alkoxyl substituent and at least one hydrocarbyl substituent directly bonded to the silicon atom. The term "silicate source" as used herein refers to substances which can be deemed as a salt form or an ester form of orthosilicic acid, for example sodium orthosilicate, sodium metasilicate, tetraethyl orthosilicate (tetraethoxysilane, TEOS), tetramethylorthosilicate, or tetrapropylorthosilicate. Optionally, the hydrocarbyl substituent can be further substituted or interrupted with a heteroatom.

In the present invention, the term "hydrocarbyl" as used herein refers to a monovalent radical derived from hydrocarbons. The term "hydrocarbon" as used herein refers to a molecule that consists of carbon and hydrogen atoms only. Examples of the hydrocarbons include, but are not limited to, (cyclo)alkanes, (cyclo)alkenes, alkadienes, aromatics, etc. When the hydrocarbyl is further substituted as mentioned above, the substituent can be halogens, amino groups, a hydroxy group, a thiol group, etc. When the hydrocarbyl is interrupted with a heteroatom as mentioned above, the heteroatom can be S, O or N. In the present invention, a hydrocarbyl preferably comprises 1 to 30 C atoms.

In the present invention, the term "alkyl" refers to a saturated, straight or branched alkyl, which comprises preferably 1-30 carbon atoms, and more preferably 1-20 carbon atoms. Examples of alkyl include, but are not limited to, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or the like.

In the present invention, the term "alkylene" refers to a divalent radical of an alkyl as noted above. The term "short chain" represents that the radical or repeating unit contains at most 6 carbon atoms in the main chain, preferably at most 4 carbon atoms.

In the present invention, the term "alkoxyl" or "alkoxy" as used herein means a group having a formula "—O-alkyl," wherein the definition of the "alkyl" in said formula has the meaning of "alkyl" as stated above.

In the present invention, the term "cycloalkyl" as used herein means a saturated or partially unsaturated cyclic carbon radical containing 3 to 10 ring carbon atoms and more preferably 3 to 8 ring carbon atoms, and optionally an alkyl substituent(s) on the ring. Examples of cycloalkyl include, but are not limited to, cyclopropyl, cyclopropenyl, cyclobutyl, cyclopentyl, cyclohexyl, 2-cyclohexen-1-yl, and the like.

In the present invention, the term "halogen" or "halo" denotes fluorine, chlorine, bromine or iodine.

In the present invention, the term "amino" as used herein means a functional group of the formula —$NR_1R_2$, wherein $R_1$ and $R_2$ each independently represent hydrogen or a hydrocarbyl group as defined above.

In the present invention, the expression "internal surface" refers to the surface of the "wall" defining the pore, and the expression "outer surface" refers to the surface of the outermost layer, wall or structure of the nanoparticles.

In the present invention, the term "therapeutic agent" as used herein refers to a substance having a therapeutic effect in an organism. Examples of the therapeutic ingredient include, but are not limited to, a small molecule drug, a protein such as an enzyme and a protein drug, an antibody, a vaccine, an antibiotic or a nucleotide drug.

In the present invention, the term "taxane-based chemotherapeutic drug(s)," or interchangeably, "taxane-based chemotherapeutic agent(s)," as used herein refers to chemically and therapeutically active compounds having a core structure of taxane or a core structure derived (such as dehydrogenation, etc.) from taxane. Examples of the taxane-based chemotherapeutic drugs/taxane-based chemotherapeutic agents include, but are not limited to, paclitaxel (PTX), cabazitaxel (CTX) and docetaxel (DTX).

Brain Cancers or Brain Metastasis

Brain cancer is a devastating disease due to the high recurrence rate and the lethal outcome despite significant recent advances in diagnostic and therapeutic modalities. Brain cancers can either originate in the brain (primary brain tumor) or spread to the brain from another part of the body (metastatic tumor). Prognoses of primary and metastatic brain cancer patients are generally poor. The median survival duration, after starting treatment, including surgery, radiation, chemotherapy, and combinations thereof, is less than a year. For instance, glioblastoma, one form of primary brain cancers, could recur within the peritumoral region while the BBB, in particular BBTB, is still intact. This significantly limits the efficacy of chemotherapeutics to erase the remaining infiltrating cancer cells. Temozolomide (TMZ) is a first-line chemotherapeutic agent for treating glioblastoma (GBM), a high-grade glioma. Unfortunately, over 50% of GBM patients do not respond to TMZ therapy. Resistance to TMZ often becomes the limiting factor in effective treatment, and nearly all patients undergo disease progression. Effective chemotherapy for GBM and TMZ refractory GBM treatment is sorely needed. To date, only a few drugs have been approved for the treatment of brain cancers. In addition, even if a patient, suffered from a cancer other than a primary brain tumor, the cancer can still spread to the brain. Those most likely to cause brain metastasis are carcinoma or cancers of lung, breast, prostate, colon, kidney, melanoma, and thyroid gland. The incidence of metastatic brain cancers is five times higher than primary brain cancers and the three most common metastatic cancers are lung (20-56% of patients), breast (5-20%), and melanoma (7-16%). Once a tumor has metastasized into the brain, neither surgery nor radiation therapy is especially effective, and the patient's chance of survival diminishes precipitously (the median overall survival is 6 months). Systemic chemotherapies are treatment options for brain metastases, but traditional chemotherapeutic agents have limited efficacy because of the BBB, in particular BBTB. To a significant extent, dealing with the issue of the BBB, in particular BBTB, which blocks the entries of most chemotherapeutic agents, would be more important than considering whether brain tumor cells would be inherently resistant to them.

The BBB is a vital physiological barrier in the central nervous system that restricts the movement of ion and molecule from circulating blood into brain and protects the brain from invading pathogens and toxic agents. However, the BBB is also challenging with respect to treating brain disease since most drugs will be hindered by the BBB. For the treatment of brain cancers, particular consideration should be given to the issue of crossing the BBTB. The existing methods for overcoming the BBB, in particular the BBTB, are still limited. For example, versatile nanoparticles with smaller size and functionalized surface can be considered as an option for crossing the BBB, in particular the BBTB; however, the effect of these diverse characteristics of nanoparticle on regulating penetration of the BBB, in particular the BBTB, remains unclear.

Surprisingly, the inventors found that MSNs with specific characteristics can effectively deliver chemotherapeutics to the main tumors and peritumoral region of the brain. For using MSNs to cross the BBB, in particular BBTB, and treat a brain tumor or CNS disease, the fine controls over the particle size (particle diameter (TEM) and hydrodynamic diameter (DLS)) and surface properties (charge, functional group, etc.) of the nanoparticle turn out to be critical. In the present invention, the inventor discloses the MSNs with specific internal surface modification of pores and optimized surface modification of particles exhibit excellent loading capacity of taxane-based chemotherapeutic drugs, e.g., PTX, DTX and CTX, good dispersity in buffer or physiological conditions, and good stability in storage or physiological conditions that can be used for BBB, in particular BBTB, penetration, brain cancer, and brain metastases treatment. In addition, drug-loaded MSN can exhibit unique anti-cell migration activity for preventing, inhibiting, or suppressing cancer metastases to offer a new remedy for metastatic brain cancer treatment. In one embodiment, the MSNs loaded with a drug can be used for the prevention or treatment of brain cancer or brain metastasis. In one embodiment, the MSNs loaded with a drug can be used for the prevention or treatment of a single form of brain cancers, a single form of brain metastases, multiple forms of brain cancers, multiple forms of brain metastases or any combinations thereof. In one embodiment, the MSNs loaded with a drug can be used for the prevention or treatment of a single form of brain metastases. In one embodiment, the MSNs loaded with a drug can be used for the prevention or treatment of multiple forms of brain cancers. In one embodiment, the MSNs loaded with a drug can be used for the prevention or treatment of multiple forms of brain metastases. In one embodiment, the MSNs loaded with a drug can be used for the prevention or treatment of multiple forms of brain cancers, multiple forms of brain metastases or combinations thereof.

In one embodiment, the brain cancer is resistant to existing drugs, as indicated, for example in information announced by the National Cancer Institute, e.g., website pages published in 2021, "Drugs Approved for Brain Tumors." In one embodiment, the brain cancer is resistant to a drug selected from the group consisting of temozolomide (TMZ), bevacizumab, belzutifan, carmustine, everolimus, lomustine and naxitamab-gqgk.

Taxane-Based Chemotherapeutic Drugs; Paclitaxel (PTX), Docetaxel (DTX) and Cabazitaxel (CTX)

As discussed herein, certain patients having brain cancers may not be effectively treated with existing drugs (such as TMZ), because rapid development of drug-resistance often limits the usefulness of existing drug in clinics. PTX, DTX and CTX may be effective against glioma cells in vitro, but have no or only marginal activity in clinical trials. To overcome the problems noted above, the inventors turned to three potential drugs for treating brain cancers: PTX, DTX and CTX.

A commonly used chemotherapeutic drug, PTX, has been approved for treating ovarian cancer, breast cancer, non-small cell lung cancer, and AIDS-related Kaposi sarcoma, but there is no market approval for treating brain cancer. PTX is a substrate of the multidrug resistance protein p-glycoprotein (p-gp) which is abundantly expressed in certain cancer cells and brain endothelial cells and is responsible for the prevention of drug accumulation in the tumor or brain, by acting as efflux pump. The inefficient penetration and accumulation of PTX in brain tumors results in no or limited efficacy in recurrent malignant glioblastoma in clinical trials. Docetaxel has been approved for treating breast cancer, non-small cell lung cancer, prostate cancer, gastric adenocarcinoma, and head and neck cancer, but there is no approval for treating brain cancer.

In addition, though it is found that DTX exhibits effective inhibition of growth glioma cells in vitro, it exhibits poor intrinsic blood-brain-tumor barrier (BBTB) permeability and off-target cytotoxic effect, which have led to no or significantly limited therapeutic success on recurrent malignant glioblastoma in clinical trials.

Hence, there is still need for development in technologies for efficiently and effectively delivering PTX or DTX to treat brain tumors.

On the other hand, CTX has been approved for treating metastatic castration-resistant prostate cancer (mCRPC), but there is no approval for treating brain cancer. The methyl group modification of CTX reduces the affinity with P-glycoprotein (P-gp) and has been used to treat paclitaxel or docetaxel-resistant cancers. In addition, CTX may have a chance to cross the blood-brain barrier. Recent studies show that applying CTX to patients with TMZ refractory glioblastoma (GBM) only exhibits limited efficacy of treatment.

Though PTX and DTX have been found ineffective against recurrent malignant glioblastoma under current experimental results, as mentioned above, and CTX only exhibits limited efficacy, they still may have potential for treating brain cancer if the problem of crossing the blood-brain barrier (BBB) or blood-brain-tumor barrier (BBTB) can be overcome. PTX, DTX and CTX have poor aqueous solubility, and the inclusion of detergents in their formulations (e.g. Cremophor EL, polysorbate 80) has been implicated in a number of systemic adverse reactions (e.g., hypersensitivity, non-allergic anaphylaxis, rash), thus requiring an inconvenient multi-step dilution process before use.

Mesoporous Silica Nanoparticles (MSNs) Loaded with Taxane-Based Chemotherapeutic Drugs There have been limited disclosures regarding loading drugs, in particular taxane-based chemotherapeutic drugs, on MSNs or other nano-delivery system for the treatment of brain cancers. Among that, a few PTX, DTX and CTX intravenous injectable nanoformulations have been developed for the treatment of brain cancers and exhibit varying degrees of effectiveness in animal studies. For example, polymeric micelles/nanoparticles (e.g., dextran-based), PLGA-coated MSN, and lipid-coated MSN loaded with PTX, and polymeric micelles/nanoparticles (e.g., PLA-PEG, PLGA-PEG nanoparticles), solid lipid nanoparticles and albumin-lipid nanoparticles loaded with DTX, and polymeric nanoparticles and liposomes loaded with CTX were used in in vivo brain tumor animal model tests, while there seems to be limited research conducted on the taxane-based chemotherapeutic drugs, including PTX-, DTX- and CTX-loaded MSNs for the treatment of brain cancers. As mentioned above, in most nanoparticles, the hydrodynamic size of the particles (measured in an aqueous or physiological medium) exceeds 100 nm, and targeting ligands may be necessary to facilitate the penetration of BBB/BBTB. However, those nanoparticles or nanoformulations may have issues that would affect the efficacy. In particular, the particles having larger particle hydrodynamic sizes may exhibit less or no efficiency in crossing BBB/BBTB. Further, upon exposure in biological fluids, serum proteins may be adsorbed onto the outer surface of nanoparticles, thereby forming a biomolecular layer and leading to a new physicochemical identity, i.e., so-called "protein corona." In addition, nanoparticles having targeting ligands on the outer surface would more easily attract protein onto the surface than the nanoparticles merely shielded with common PEGylation modification. This biomolecular layer (corona layer) surrounding the nanoparticles would interfere with targeting molecules on the surface of nanoparticles and may even cause agglomeration and higher opsonization, leading to mistargeting or unintended scavenging by the liver, kidney, or spleen, thereby exhibiting potential, undesired side effects or reduced therapeutic efficacy. The nanoformulations with larger particle hydrodynamic sizes and targeting ligands on the surface may encounter obstacles, as mentioned above, and thus lead to insufficient or little efficacy in brain cancer treatment, which may not be successfully translated from bench to in vivo or clinical applications. In fact, to date, none of them has been approved in the market.

To prevent or solve the problems, the inventors inferred that, with certain surface modifications, MSNs may have potentials in providing the desired pharmacological effect, such as EPR effect and BBB, in particular BBTB, penetration properties, and can be used for loading taxane-based chemotherapeutic drugs, e.g., PTX, DTX and CTX. Specifically, mesoporous silica nanoformulation of taxane-based chemotherapeutic drugs, e.g., DTX, for injectable suspension (DTX@MSN), offers multiple benefits, including but not limited to: (1) enhancing DTX "solubility" without using detergents that have been implicated in many systemic adverse reactions of the current DTX formulation in clinical use; (2) diminishing drug-related adverse effects; (3) increased BBTB penetration and tumor-targeting ability of DTX; the DTX@MSN thus can prolong remission and survival of patients with malignant glioblastoma multiforme. Various MSNs can be used in this invention for loading drugs. MSNs can also be modified with a variety of surface functional groups to improve their biocompatibility and design for different purposes. For example, the inventors use the MSNs having surface modification with (i) an organic molecule, oligomer or polymer and (ii) a positively charged molecule, oligomer or polymer, and pore internal surface modification with a terminal hydrocarbyl moiety, to load taxane-based chemotherapeutic drugs, e.g., PTX, CTX or DTX. In one embodiment, the MSNs with specific surface modifications (e.g. PEGylation, positive charge modification, etc.) exhibit smaller particle sizes, especially smaller hydrodynamic sizes in aqueous, physiological solutions, and customized surface charge, which may decrease the protein corona adsorption and prolong circulation time and the capability of brain tumor targeting to enhance the efficacy of treatment of brain cancers. In connection with this, the MSNs used in the claimed invention do not have any "targeting ligand" toward brain cancer or tumor, or receptors on the cell membrane, etc. The targeting ligands include, but are not limited to, targeting peptide, targeting nucleotide, targeting protein, targeting antibody, targeting antigen, etc.

Examples of the organic molecule, oligomer or polymer (i) include, but are not limited to, short-chain poly(alkylene glycol)(PAG), e.g., poly(ethylene glycol) (PEG), poly(propylene glycol) (PPG), PEG-PPG copolymers, etc. Further (organic) modifying agents can be introduced to modify the properties of MSNs (e.g., surface properties, etc.); examples thereof include, but are not limited to, mercapto propyl trimethoxysilane, chloro methyl trimethoxysilane, ethyltriacetoxysilane (ETAS), N-(trimethoxysilylpropyl)ethylenediaminetriacetic acid (EDTAS), (3-trihydroxysilyl)propyl methylphosphonate (THPMP), methyltriacetoxysilane (MTAS), (3-mercatopropyl)trimethoxysilane (MPTMS), zwitterionic silane, etc.

Examples of the positively charged molecule, oligomer or polymer (ii) include, but are not limited to, polyethylenimine (PEI); alkoxysilane-terminated (poly)alkylene(poly)amine, such as N-[3-(trimethoxysilyl)propyl]-N,N,N-trimethylammonium chloride (TA), N-[3-(Trimethoxysilyl)propyl]ethylenediamine (EDPTMS), $N^1$-(3-Trimethoxysilylpropyl)diethylenetriamine, etc.; organo-alkoxysilane such as 3-aminopropyltrimethoxysilane (APTMS), 3-aminopropyl triethoxysilane, etc.

In certain cases, it would be necessary to use a positively charged molecule, oligomer or polymer (ii) having a length shorter than the organic molecule, oligomer or polymer (i) when making the surface modification, which is believed to reduce non-specific binding toward a non-target.

Examples of the terminal hydrocarbyl moiety include, but are not limited to, a terminal aromatic moiety, a terminal (cyclo)aliphatic moiety or combinations thereof. The expression "terminal" implies that the hydrocarbyl moiety is directly linked to the silicon atom of the silica nanoparticle. In some embodiments, the terminal aromatic moiety is substituted with lower alkyl, or halogen. In a further embodiment, the terminal aromatic moiety is derived from trimethoxyphenylsilane (TMPS). In some embodiments, the terminal (cyclo)aliphatic moiety comprises (cyclo)alkyl, (cyclo)alkenyl or combinations thereof, which can be optionally substituted with lower alkyl or halogen. In one embodiment, the terminal aliphatic moiety is derived from long-chain alkyl silanes with 4 to 18 carbon atoms, which include, but are not limited to, butyltrimethoxysilane, butyltriethoxysilane, hexyltrimethoxysilane, hexyltriethoxysilane, octyltrimethoxysilane, octyltriethoxysilane, iso-octyltrimethoxysilane, iso-octyltriethoxysilane, dexyltrimethoxysilane, dexyltriethoxysilane, dodexyltrimethoxysilane, dodexyltriethoxysilane, tetradecyltrimethoxysilane, tetradecyltriethoxysilane, hexadecyltrimethoxysilane, haxadecyltriethoxysilane, octadecyltrimethoxysilane, and octadecyltriethoxysilane, preferably trimethoxy$C_{6-8}$alkylsilane.

The inventors found that certain problems should preferably be solved when loading taxane-based chemotherapeutic drugs, e.g., PTX, CTX or DTX on the MSNs. For example, if the surface modification with (i) and (ii) noted above is too high, then the loading efficiency would be severely affected. Another challenge would be the suspensibility and stability of the nanoparticles with pore internal modification of terminal hydrocarbyl moiety. The inventors then surprisingly found that, the MSNs having surface modification with (i) and (ii) noted above, with the molar ratio of (i) and (ii) ranging from 60:1 to 4:1, e.g., from 55:1 to 4.5:1, 50:1 to 5:1, 45:1 to 5.5:1, 40:1 to 5.5:1, 35:1 to 5.5:1, 30:1 to 5.5:1, 25:1 to 5.5:1, 20:1 to 5.5:1, 15:1 to 5.5:1, 12.5:1 to 4.5:1, 10:1 to 5:1, 8.5:1 to 5.5:1, 7.5:1 to 6.5:1, or being about 7:1, or any numeric ranges consisting of the above-mentioned endpoints, such as 55:1 to 7:1, 20:1 to 6.5:1, 45:1 to 7:1, etc., could greatly improve the issues. The molar ratio of (i) and (ii) can be determined by elemental analysis, or from the reagents used in the preparation of MSNs. In addition, the inventors found that the amount of terminal hydrocarbyl moiety (on the pore surface) should be large enough to improve the loading efficiency of taxane-based chemotherapeutic drugs, e.g., PTX, DTX or CTX. In one embodiment, pore surface modification can be achieved by using a silane(s) having no terminal hydrocarbyl moiety and a silane(s) having at least one terminal hydrocarbyl moiety, wherein the terminal hydrocarbyl moiety comes from the silane(s) having at least one terminal hydrocarbyl moiety. In one embodiment, the amount of terminal hydrocarbyl moiety used in the preparation of MSNs expressed by the molar ratio of the silane(s) having no terminal hydrocarbyl moiety to the silane(s) having at least one terminal hydrocarbyl moiety is at least 50:1, or at least 40:1, at least 35:1, at least 30:1, at least 25:1, at least 20:1, at least 15:1, at least 10:1, at least 5:1 or within any numeric ranges consisting of the endpoints noted above, e.g., from 5:1 to 50:1, from 15:1 to 50:1, from 20:1 to 40:1, etc. In one embodiment, calculation and/or measurements can be made to obtain the number of silanes having at least one terminal hydrocarbyl moiety per particle.

In one specific embodiment, when used for loading taxane-based chemotherapeutic drugs, e.g., PTX, CTX or DTX, the inventors found that the MSNs may have an outer surface modification with (i) an organic molecule, oligomer or polymer and pore internal surface modification with a terminal hydrocarbyl moiety, but without outer surface modification with (ii) a positively charged molecule, oligomer or polymer, and the drug-loaded MSNs still can exhibit the desired properties.

In one embodiment, the mesoporous silica nanoparticle of the present disclosure has an average particle size of 60 nm or less, 50 nm or less, 40 nm or less, 30 nm or less, or 20 nm or less, measured by TEM. In one embodiment, the mesoporous silica nanoparticle of the present disclosure has a pore size of 50 nm or less, 45 nm or less, 40 nm or less, 35 nm or less, 30 nm or less, 25 nm or less, 20 nm or less, 15 nm or less, 10 nm or less, 5 nm or less, or 3 nm or less, or any numeric ranges consisting of the endpoints noted above, such as from 3 nm to 50 nm, 5 nm to 35 nm, 10 nm to 45 nm, etc. In one embodiment, the mesoporous silica nanoparticle of the present disclosure has an average dynamic light scattering particle size of 60 nm or less, 50 nm or less, 40 nm or less, or 30 nm or less measured in phosphate buffered saline (PBS) by dynamic light scattering. Without being bound to the theory, an average DLS size in PBS of the (drug loaded) mesoporous silica nanoparticle of 60 nm or less would be helpful both for intravenous administration of the nanoformulation and the penetration of BBB/BBTB.

In certain embodiments, the zeta potential (in pH 7.4 condition) of the MSNs may range from −22 to +25 mV, −20 to +20 mV, −15 to +15 mV, or −10 to +10 mV, or a reasonable numeric range within the endpoints mentioned herein, for example −15 to +20 mV, −10 to +25 mV, −15 to +10 mV, etc. In one embodiment, the mesoporous silica nanoparticle has a BET surface area of 1000 $m^2$/g or less, 750 $m^2$/g or less, or 500 $m^2$/g or less or 250 $m^2$/g or less.

In one embodiment, the taxane-based chemotherapeutic drug is selected from the group consisting of paclitaxel (PTX), cabazitaxel (CTX), docetaxel (DTX) and any combinations thereof. In one embodiment, the taxane-based chemotherapeutic drug is selected from the group consisting of CTX, DTX and a combination thereof. In one embodiment, the taxane-based chemotherapeutic drug is selected from the group consisting of PTX, CTX and a combination thereof. In one embodiment, the taxane-based chemotherapeutic drug is selected from the group consisting of PTX, DTX and a combination thereof. In one embodiment, the taxane-based chemotherapeutic drug is DTX. In one embodiment, the taxane-based chemotherapeutic drug is PTX. In one embodiment, the taxane-based chemotherapeutic drug is CTX.

The mesoporous silica nanoparticle has at least one of the following characteristics:
  (a) surface modification with (i) an organic molecule, oligomer or polymer and (ii) a positively charged molecule, oligomer or polymer, wherein the molar ratio of (i) and (ii) ranges from 60:1 to 4:1;
  (b) pore internal surface modification with a terminal hydrocarbyl moiety;
  (c) an average particle size of 60 nm or less, measured by TEM;
  (d) an average dynamic light scattering particle size of 60 nm or less, measured in phosphate buffered saline (PBS) by dynamic light scattering; and
  (e) surface modification with (i) an organic molecule, oligomer or polymer.

In one embodiment, the MSN has characteristics (a) and (b); characteristics (e) and (b); or characteristics (b) and (d); preferably has characteristics (a), (b) and (c); preferably has characteristics (e), (b) and (c); preferably has characteristics (a), (b) and (d); preferably has characteristics (e), (b) and (d); preferably has characteristics (b), (c) and (d); more preferably has characteristics (a), (b), (c) and (d); and more preferably has characteristics (e), (b), (c) and (d).

MSN loaded with taxane-based chemotherapeutic drugs, e.g., PTX, CTX or DTX, which exhibits BBB, in particular BBTB, penetration capability will show advantages in being a high potential drug delivery system for treating brain associated cancers. All the examples, ingredients, reaction conditions or parameters illustrated in the examples are merely for illustration purposes and are not intended to limit the material or the preparation method by the exemplary embodiments described herein.

Mesoporous silica nanoparticles (MSNs) possess well-defined structures and high density of surface silanol groups which can be modified with a wide range of organic functional groups. The different sizes of MSNs are prepared using an ammonia base-catalyzed method. The particle size is controlled by adjusting ammonia concentration, amount and concentration of the silane source, reaction temperature, etc.

In order to arrive at the desired characteristics of the MSNs for loading taxane-based chemotherapeutic drugs (e.g., PTX, DTX or CTX) (e.g., loading capacity, dispersity, and stability), the inventors conducted critical trials to modify the synthesis procedure of MSNs, including but not limited to (1) introducing the concept of sequential additions of silane source and internal surface modulating agent; specifically, the internal surface modulating agent is introduced before the addition of silane source; (2) adjusting the ratio and amounts of silane source/internal surface modulating agent (internal surface modification); (3) adjusting the ratio and amounts of (i) the organic molecule, oligomer or polymer and (ii) the positively charged molecule (external surface modification); and (4) adjusting hydrothermal conditions, including temperature, duration of heating, etc.

Without being bound to the theory, the modifications (1) and (4) may elevate the structural robustness and aqueous dispersity/suspension stability of MSN; the modifications (1) and (2) may increase drug loading capacity and particle stability; and the modification (3) may improve the dispersity of particles in aqueous solution, in particular physiological media, and reduce the pore blockage caused by, e.g., the positively charged molecule (which may lead to reduction of drug loading capacity).

In the present disclosure, drugs can thus be loaded within the pores rather than attached to the outer surface of MSN, resulting in no significant difference in DLS sizes of MSN before and after drug loading. In summary, this invention overcomes the unexpected deficiencies of existing MSNs by providing smaller hydrodynamic size, good dispersity, and stability of drug-loaded MSN, which are all critical for MSNs as a carrier loading taxane-based chemotherapeutic drugs, e.g., PTX, DTX and CTX, especially in applications of intravenously administered nanomedicine.

In one embodiment, the difference in DLS size (e.g., measured at 37° C. in PBS) of drug loaded MSN after overnight incubation (e.g., 15 to 24 hours) would be less than 10 nm, preferably less than 5 nm.

In one aspect, MSNs can be prepared with a method comprising the following steps: (a) providing an alkaline solution containing a surfactant at a concentration sufficient for forming micelles; (b) introducing a silane source(s) into the solution; (c) introducing (i) an organic molecule, oligomer or polymer and optionally (ii) a positively charged molecule, oligomer or polymer into the solution; (d) conducting hydrothermal treatment on the solution; (e) collecting the products; (f) removing the residual surfactant(s) from the products; and optionally (g) purifying or cleaning the products. In one embodiment, the method comprises step (b-1), as step (b), introducing a silane with hydrocarbyl moiety silane having at least one terminal hydrocarbyl moiety then introducing silane source(s), preferably step (b-1-1) sequentially introducing the a silane with hydrocarbyl moiety silane having at least one terminal hydrocarbyl moiety, a first part of the silane sources and a second part of the silane sources. In one embodiment, the method comprises step (c-1), as step (c), introducing components (i) and (ii) indicated above in step (c). In one embodiment, the method comprises step (d-1), as step (d), conducting sequential hydrothermal treatment on the solution at a first temperature in a first period and a second temperature in a second period. In various embodiments, the method comprises steps (a) to (g); steps (a), (b-1)/(b-1-1), (c) to (f); steps (a), (b-1)/(b-1-1), (c) to (g); steps (a), (b), (c-1) to (f); steps (a), (b), (c-1), (d) to (g); steps (a) to (c), (d-1), (e), (f); steps (a) to (c), (d-1), (e) to (g); steps (a), (b-1)/(b-1-1), (c-1), (d) to (f); steps (a), (b-1)/(b-1-1), (c-1), (d) to (g); steps (a), (b-1)/(b-1-1), (c), (d-1), (e), (f); steps (a), (b-1)/(b-1-1), (c), (d-1), (e) to (g); steps (a), (b), (c-1), (d-1), (e), (f); steps (a), (b), (c-1), (d-1), (e) to (g); steps (a), (b-1)/(b-1-1), (c-1), (d-1), (e), (f); or steps (a), (b-1)/(b-1-1), (c-1), (d-1), (e) to (g).

Typically, 0.2 to 0.5 g of a surfactant was dissolved in 150 to 250 mL of an aqueous, alkaline solution (e.g., ammonium hydroxide solution (0.1 to 0.25M)) at the desired temperature (45 to 65° C.) in a sealed beaker. After 10 to 30 minutes of stirring, 15 to 135 µL of a silane having at least one terminal hydrocarbyl moiety in 60 to 500 µL of a solvent (e.g., alcohol, such as ethanol) was added and stirred for 20 to 60 minutes. After that, the sealed membrane was removed, and then 150 to 750 µL of a silane having no terminal hydrocarbyl moiety in 0.8 to 3 mL of a solvent (e.g., alcohols, such as ethanol) was added to the solution under stirring, preferably vigorous stirring. After 0.5 to 1.5 hours of stirring, another 100 to 500 µL of a silane having no terminal hydrocarbyl moiety in 0.4 to 2 mL of a solvent (e.g., alcohol, such as ethanol) was added. After 2 to 4 hours of the reaction, 825 to 1700 µL of PEG-silane (a silane having PEG moiety, e.g., (2-[methoxy(polyethyleneoxy)$_{6-9}$propyl]- trimethoxysilane)) with 0 to 455 μL a positively charged molecule, oligomer or polymer (e.g., TA-silane, (N-[3-(trimethoxysilyl)propyl]-N,N,N-trimethylammonium chloride)) in 2.5 to 5.4 mL of a solvent (e.g., alcohols, such as ethanol) was introduced into the reaction. Then optionally, another 0 to 85 μL TEOS in 0 to 500 μL EtOH was immediately added. After the mixture was stirred for 0.5 to 1.5 hours, it was aged at the desired temperature (e.g., 45 to 65° C.) without stirring for at least 12 hours. Then, the solution was sealed and placed in an oven at 65 to 75° C. for 40 to 60 hours or at 65 to 75° C. and at 85 to 95° C. each for 20 to 28 hours of hydrothermal treatment. The as-synthesized product was washed and collected by centrifugation or cross-flow system. For removing the surfactant from the pores of the MSNs, the as-synthesized product was incubated in 40 to 85 mL of acidic solvent (e.g., alcohols, such as ethanol) containing an acid (such as hydrochloric acid (37%)) for 0.5 to 1.5 hours of extraction at 55 to 65° C., and the incubation was conducted once or several times. The products were washed and harvested by centrifugation or cross-flow system and finally stored, preferably in 85% or higher ethanol. For different functional group modified MSN-PEG synthesis, different positively charged molecules, oligomers or polymers, such as TA-silane, EDPTMS-silane or other functional-silanes were used. In one instance, the molar ratio of TEOS/octyltriethoxysilane varied from 50:1 to 5:1, e.g., 35:1 to 8:1, 30:1, 20:1, 15:1, and 10:1, and the ratio of PEG-silane/TA-silane varied from 18:1 to 4:1, e.g., 15:1, 10:1, 7:1, 4:1 and n:0 (i.e., PEG only) to provide different levels of modification.

In one embodiment, the silane source comprises tetraethoxysilane (TEOS), tetramethoxysilane (TMOS), sodium silicate or a mixture thereof. Surface modifying agents can be used for adjusting the properties of MSNs. In one embodiment, the (organic) modifying agent(s) includes, but is not limited to, propyl triethoxysilane, butyl trimethoxysilane, octyltrimethoxysilane, diphenyl diethoxysilane, n-octyltriethoxysilane, mercapto propyl trimethoxysilane, chloro methyl trimethoxysilane, isobutyl triethoxysilane, ethyl trimethoxy styrene silane, methyl triethoxysilane, phenyltriethoxysilane (PTEOS), phenyltrimethoxysilane (PTMOS), methyltrimethoxysilane (MTMOS), ethyltriacetoxysilane (ETAS), N-(trimethoxysilylpropyl)ethylenediaminetriacetic acid (EDTAS), (3-trihydroxysilyl)propyl methylphosphonate (THPMP), methyltriacetoxysilane(MTAS), (3-mercaptopropyl)trimethoxysilane (MPTMS), zwitterionic silane, (N-[3-(trimethoxysilyl)propyl]-N,N,N-trimethylammonium chloride), N-[3-(Trimethoxysilyl)propyl]ethylenediamine, polyethylenimine (PEI); alkoxysilane-terminated (poly)alkylene(poly)amine, or organo-alkoxysilane with amino group(s), etc.

Examples of surfactants suitable for preparing MSNs include, but are not limited to, cationic surfactants, anionic surfactants and non-ionic surfactants. Proper surfactants are selected based on the conditions of reaction, such as pH value, ionic strength, temperature, reactants and products, etc. Examples of cationic surfactants include, but are not limited to, pH-dependent primary, secondary, or tertiary amines with a long-chain hydrocarbyl group, and the terminal amine group bears positive charge when presenting below a specific pH value, such as primary and secondary amines becoming positively charged at pH<10, for example octenidine dihydrochloride; and permanently charged quaternary ammonium salts, e.g., cetrimonium bromide (CTAB), cetylpyridinium chloride (CPC), benzalkonium chloride (BAC), benzethonium chloride (BZT), dimethyldioctadecylammonium chloride, and dioctadecyldimethyl-ammonium bromide (DODAB). Examples of anionic surfactants include, but are not limited to, sulfate, sulfonate, and phosphate salts or esters; such as ammonium lauryl sulfate, sodium lauryl sulfate (sodium dodecyl sulfate, SLS, or SDS), and the related alkyl-ether sulfates, sodium laureth sulfate (sodium lauryl ether sulfate or SLES), and sodium myreth sulfate, docusate (dioctyl sodium sulfosuccinate), perfluorooctanesulfonate (PFOS), perfluorobutanesulfonate, alkyl-aryl ether phosphates, alkyl ether phosphates, etc. Examples of non-ionic surfactants include, but are not limited to, poly(oxyethylene)nonylphenyl ether, polyoxyethylene glycol sorbitan alkyl ester, polyethylene glycol alkyl ether, glucoside alkyl ether, polyethylene glycol octylphenyl ether, polyethylene glycol alkylphenyl ether, glycerol alkyl ester, polypropylene glycol alkyl ethers, block copolymers, poloxamers, cocamide MEA, cocamide DEA, lauryldimethylamine oxide or polyethoxylated tallow amine.

Size of MSNs

The different sizes of MSNs may be prepared by using an ammonia base-catalyzed method. In one aspect, the MSNs are prepared under highly diluted and low surfactant conditions. In the present disclosure, MSNs preferably have an average diameter of less than 40 nm, measured by TEM. Control of the size of MSNs can be achieved by adjusting the ammonia concentration, amount and concentration of alkoxysilane, reaction temperature, etc. Without being bound to the theory, when the ammonia concentration is higher, the size of MSNs may become larger and vice versa; when the amount of alkoxysilane is larger, the size of MSNs may become larger and vice versa. In various embodiments, 0.14-0.5 g CTAB in 150 mL ammonium hydroxide solution is used, the ammonia concentration ranges from 0.05 to 1.5M, preferably from 0.1 to 0.5 M, more preferably from 0.1 to 0.25 M; the amount of alkoxysilane added into 150 mL ammonium hydroxide solution ranges from 1 mL to 5 mL, preferably from 1 mL to 3 mL, more preferably from 2 mL to 2.5 mL of ethanolic TEOS (i.e., TEOS in ethanol, about 0.862 to 1.2M); and the reaction temperature ranges from 30° C. to 60° C., preferably from 40° C. to 60° C., more preferably from 50° C. to 60° C.; any combination of these conditions may serve as an embodiment of the present disclosure.

Additional Active Agent

For the treatment of disease, at least one additional bioactive ingredient (active agent) can be loaded onto and/or into MSNs, for example distributed within the space in MSNs, on the surface of MSNs, etc. The additional bioactive ingredient may be properly selected based on the size thereof and the disorders/diseases concerned. In certain embodiments, the additional bioactive ingredient is co-administered with, administered prior to or administered after the administration of taxane-based chemotherapeutic drug loaded MSN. Examples of the additional bioactive ingredient include, but are not limited to, everolimus, trabectedin, abraxane, TLK 286, AV-299, DN-I01, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trapantibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-I00380, sunitinib,5-fluorouracil, vorinostat, etoposide, gemcitabine, doxorubicin, liposomal, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1-H-pyrrolo[2,3-d]pyrimidin-5-yl)ethyl]benzoyl]-disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, goserelin acetate, leuprolide acetate, triptorelinpamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanibcanertinib, ABX-EGF antibody, erbitux, EKB-569, PKI-166, GW-572016, Ionafarnib, BMS-214662, tipifamib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, Bacillus Calmette Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, etc., fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracilmustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukindiftitox, gefitinib, bortezimib, paclitaxel, cremophor-free paclitaxel, epithilone B,BMS-247550, BMS-310705, droloxifene,4-hydroxytamoxifen, pipendoxifene,ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl) rapamycin, temsirolimus, AP-23573, RAD001, ABT-578, BC-210, LY294002, LY292223, LY292696, LY293684, LY293646, wortmarmin, ZM336372, L-779,450, PEG-filgrastim, darbepoetin, erythropoietin, granulocytecolony-stimulating factor, zolendronate, prednisone, cetuximab, granulocyte macrophage colony-stimulating factor, histrelin, pegylated interferon alfa-2a, interferon alfa-2a,pegylated interferon alfa-2b, interferon alfa-2b, azacitidine, PEG-L-Asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomabtiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, curcumin, curcumin analog. In one embodiment, the taxane-based chemotherapeutic drug loaded MSN is administered in combination with (temozolomide) TMZ, e.g., the TMZ being co-administered with, administered prior to or administered after the administration of taxane-based chemotherapeutic drug loaded MSN.

BBB/BBTB Penetration Effect

The blood-brain barrier (BBB) restricts most therapeutic drugs transported into the brain; when focusing on the treatment of brain cancers, particular consideration must be given to crossing the blood-brain-tumor barrier (BBTB). Nanomedicine can modulate the nanoparticle size, shape, surface charge, and/or conjugated ligands to increase penetration of the BBB or BBTB. Nanoparticle conjugated with targeting ligands that bind to receptors on endothelial cells, such as transferrin, lactoferrin, glutathione and low-density lipoprotein receptors, may also promote BBB or BBTB penetration. The present invention provides balance between the efficacy of BBB, in particular BBTB, penetration effect and loading efficiency of taxane-based chemotherapeutic drugs, e.g., PTX, CTX or DTX to achieve the optimized results in treating brain cancers.

Inhibition of Cancer Metastasis to Prevent Brain Cancer

Cancer metastasis would result in high death rate of patients suffering from a cancer. In addition, if the cancer is metastatic and transfers to the brain, then it is more difficult to treat. Hence, the subject disclosure also relates to prevention of brain cancer, which is achieved by intravenously administering the mesoporous silica nanoparticle loaded with an agent, e.g., taxane-based chemotherapeutic drugs, e.g., PTX, DTX or CTX, of the subject disclosure to a subject suffering from a metastatic cancer occurring outside the brain to prevent the metastatic cancer transfer to the brain. In one embodiment, the metastatic cancer comprises lung cancer, breast cancer, prostate cancer, colon cancer, kidney cancer, melanoma, thyroid gland cancer or any combinations thereof.

The following examples are provided to make the present invention more comprehensible to those of ordinary skill in the art to which the present invention pertains, but are not intended to limit the scope of the invention.

EXAMPLES

Materials, Methodologies and Test Models

Transmission Electron Microscope (TEM)

Transmission electron microscopy (TEM) is used to examine and verify the appearance of silica nanoparticles. TEM images were taken on a Hitachi H-7100 transmission electron microscope operated at an accelerated voltage of 100 kV. Samples dispersed in ethanol were dropped on carbon-coated copper grids and dried in air for TEM observation.

Dynamic Light Scattering (DLS) and Zeta Potential

Size measurements of the silica nanoparticles in different solution environments were performed with dynamic light scattering (DLS) on a Malvern Zetasizer Nano ZS (Malvern, UK). The (solvated) particle sizes formed in the following different solutions were analyzed: $H_2O$ and PBS buffer solution (pH7.4) at room temperature. Surface charge (zeta potential) of the silica nanoparticles in PBS (0.01×, pH 7.4) at a particle concentration of 0.1 mg/mL was performed by a Malvern Zetasizer Nano ZS.

Thermogravimetric Analysis and Elemental Analysis

Thermogravimetric analysis (TGA) was recorded from 40 to 800° C. on a thermal analyzer with a heating rate of 10° C. $min^{-1}$ in an air purge of 40 mL $min^{-1}$. The mass percentage of carbon, nitrogen, oxygen and hydrogen in silica nanoparticle was determined by elemental analyzer (elementar Vario EL cube type for NCSH, German).

Multiphoton Fluorescence Microscopy

Multi-photon microscopy (Olympus FVMPE-RS) was used to visualize the distribution of fluorescence-labeled MSN in cerebrovascular of brain tissue region and brain tumor region of U87 orthotopic xenograft tumor mice. Mice were anesthetized for the skull-removed craniotomy. The images of particle distribution were captured from the surface of brain (i.e., at a depth of about 150 um) using a two-photon microscope at an excitation wavelength of 850 nm with a water-immersion objective.

U87 Glioma Animal Model

U87-LUC glioma cells were cultured at 37° C. in a humidified 5% $CO_2$ atmosphere in minimum essential median (MEM) or Dulbecco's Modified Eagle Medium (DMEM) supplemented with 10% fetal bovine serum and 1% penicillin/streptomycin (Invitrogen). Cells were harvested by trypsinization, washed once with phosphate-buffered saline (PBS), and resuspended ($1 \times 10^5$ cell/μL; $3 \times 10^5$ cell/3 μL) in MEM or PBS for subsequent implantation into the striatum of mouse brains. Pathogen-free male NU/NU mice (5 to 7 weeks old) or Balb/c nude mice (5 to 7 weeks old, male) were purchased from BioLASCO Taiwan Co. Ltd. Mice were housed and maintained in a controlled environment, and all procedures were performed following the experimental animal care guidelines. To implant U87-LUC tumor cells, animals were anesthetized with 2% isoflurane gas or with Zoletil (20-40 mg/kg) and Xylazine (5-10 mg/kg) mixture solution and immobilized on a stereotactic frame. A sagittal incision was made through the skin overlying the calvarium, and a 23 G needle was used to create a hole in the exposed cranium 1.5 mm anterior and 2 mm lateral to the bregma. Five or three microliters of U87-LUC glioma cell suspension were injected at a depth of 2 mm from the brain surface. The injection was performed over 3 minutes, and the needle was withdrawn over another 2 minutes. The growth of the brain tumor was optionally monitored by IVIS and MRI.

TMZ-Resistant Glioma Animal Model

TMZ-resistant glioma cells (U87MG-R) were cultured at 37° C. in a humidified 5% $CO_2$ atmosphere in Dulbecco's Modified Eagle Medium (DMEM) supplemented with 10% fetal bovine serum and 100 ug/mL penicillin/streptomycin. NOD-SCID male mice (8-week-old) were purchased from BioLASCO Taiwan Co. Ltd. For intracranial transplantation, an experimental procedure was performed under sterile conditions. For TMZ-resistant glioblastoma transplantation, a skull burr hole was created in the right frontal brain area. Cells ($2 \times 10^5$, or five microliters of TMZ-resistant glioma cell suspension (U87MG-R, $6 \times 10^5$ cells/5 μL) were injected into the cortex at a depth of 3 mm using stereotactic guidance and a microprocessor single syringe (Harvard Apparatus, Holliston, MA, USA).

Example 1

Preparation of Mesoporous Silica Nanoparticles with Various Ratios of TEOS to Octyltriethoxysilane (C8-Silane) Modification on the Sidewall of Pores and Ratios of PEG to Functional Groups Modification on Nanoparticle Surface Mesoporous silica nanoparticles (MSNs) possess a well-defined structure and high density of surface silanol groups which can be modified with a wide range of organic functional groups. The MSNs of different sizes were prepared using an ammonia base-catalyzed method under highly diluted and low surfactant conditions. The particle size was controlled by adjusting ammonia concentration, TEOS amount added, and reaction temperature. TA-silane (N-[3-(trimethoxysilyl)propyl]-N,N,N-trimethylammonium chloride) was used as the exemplified charge modulating agent for providing positively charged groups on the surface of the MSNs, and octyltriethoxysilane was used as an internal surface modulating agent for providing aliphatic group on the internal surface of pores of MSNs. Typically, 0.29 to 0.49 g of CTAB was dissolved in 150 to 250 mL of ammonium hydroxide solution (0.1-0.25M) at the desired temperature (50-60° C.) in a sealed beaker. After 15-minutes of stirring, 15.6-130.5 μL of the terminal hydrocarbyl moiety (octyltriethoxysilane) with 60 to 500 (e.g., 200) L ethanol was added and stirred for 30 minutes. After that, the sealed membrane was removed, and then 150 to 750 μL TEOS in 0.8 to 3.0 mL ethanol were added to the solution under vigorous stirring. After 1 hour of stirring, another 100 to 500 μL TEOS in 0.4 to 2.0 (e.g., 0.6 to 1.3) mL ethanol was added. After 3 hours of the reaction, the PEG-silane (2-[methoxy(polyethyleneoxy)$_{6-9}$propyl]-trimethoxysilane) (850 to 1700 μL, e.g., 1000 μL) with 0 to 455 μL (e.g. 155.8 μL) TA-silane (N-[3-(trimethoxysilyl)propyl]-N,N,N-trimethylammonium chloride) in 2.6 to 5.4 mL (e.g., 3.2 mL) of ethanol was introduced into the reaction. In certain cases, another addition of up to 85 μL TEOS in up to 500 μL EtOH was immediately added. After stirring for 1 hour, the mixture was aged at the desired temperature (e.g., 50-60° C.) without stirring for at least 12 hours, until the final reaction volume lowered to 40 to 85 mL. Then, the solution was sealed and placed in an oven at about 70° C. for 40 to 48 hours, or at about 70° C. for 18 to 24 hours and at about 90° C. for another 22 to 24 hours of hydrothermal treatment. The as-synthesized sample was washed and collected by centrifugation or a cross-flow system. For removing the surfactant in the pores of the MSNs, the as-synthesized sample was incubated in 40 to 85 mL (e.g., 50 to 85 mL) of acidic ethanol containing 678 to 1442 μL (e.g., 848 μL) (first time) and 40 to 85 μL (e.g., 50 to 85 μL) (second time) of hydrochloric acid (37%) for 1 hour of extraction at 60° C. The products were washed and harvested by centrifugation or cross-flow system and finally stored in ethanol of greater than 90%, or in (pure) $H_2O$. For different functional group(s) modified MSN-PEG synthesis, the TA-silane was replaced with EDPTMS-silane or other functional-silanes. For attaining different levels of modification, the molar ratio of TEOS/octyltriethoxysilane varied from 50:1, 40:1, 30:1, 20:1, 15:1, 10:1 and 5:1, and the ratio of PEG-silane/TA-silane varied from 15:1, 10:1, 7:1, 4:1 and n:0 (i.e., PEG only).

Taxane-Based Chemotherapeutic Drugs (Docetaxel and Cabazitaxel) Loading in MSN

The C8-MSN-PEG/TA particle (about 1.6 g) was dispersed in 16 to 50 mL (e.g., 16 to 32 mL) of $H_2O$. The DTX or CTX stock solution (1.161 to 1.862 mL) with a concentration of 50 mg/mL in DMSO was used for drug loading, and it was slowly dropped into the particle solution with vigorous stirring. After the solution was fully mixed, the mixture was further diluted with $H_2O$ (48 to 50 mL) to decrease the DMSO concentration. To remove the trace amount of free drug aggregates, the mixture was filtered with 0.22 μm of filter. Next, the mixture was washed with 7 to 10-fold $H_2O$ by a cross-flow system. Finally, the product was stored in $H_2O$.

Reference Example 1

The internal surface modification of MSNs has been used for loading drugs for delivery, e.g., anti-cancer agents, such as curcumin analogs. However, particles known in the art would not be suitable for taxane-based chemotherapeutic drugs (e.g., paclitaxel, docetaxel and cabazitaxel) delivery, in particular in in vivo applications, due to their poor drug loading efficacy of taxane-based chemotherapeutic drugs, dispersity in aqueous solution and stability in storage and physiological conditions. The inventors' preliminary research showed that the dispersity of C8-silane introduced particles in PBS would be influenced by the ratio of TEOS/C8-silane in the synthesis process. For example, particles synthesized with a TEOS:C8-silane ratio=20:1 exhibit similar hydrodynamic sizes (DLS) in water and PBS. However, when we tried to increase the proportions of C8-silane (to a TEOS:C8-silane ratio=15:1) to enhance the drug loading capability, the DLS size of MSNs in PBS was twice as larger as that in water. When we tried to further increase the proportions of C8-silane to a TEOS:C8-silane ratio=10:1, severe aggregation of particles in PBS was observed, with a DLS size of about 1 μm. Furthermore, after overnight incubation in PBS at 37° C., the particles exhibited unstable dispersion and aggregation and thus were considered unstable, evidenced by the significantly increased DLS sizes, which implies that the particle structure or surface modification of MSNs may be degraded or destroyed. However, inventors are also concerned that lowering the proportion of internal organic modification (in this example, C8-silane) may affect the drug loading efficiency.

Improvement of Drug Loading Capacity, Dispersity, and Stability of Taxane-Based Chemotherapeutic Drugs@MSN, in Particular DTX@MSN and CTX@MSN Nanoformulation In order to solve the problems due to optimization of these factors (e.g., loading capacity, dispersity, and stability), as exemplified in Example 1, the inventors tried to make adjustments of, including but not limited to, the ratio of TEOS/C8-silane, hydrothermal conditions and the surface modification, etc., for MSN synthesis. In particular, for increasing drug loading capacity and particle stability, we not only increased the amount of C8-silane in synthesis process to TEOS:C8-silane=15:1 but also adjusted the addition order of TEOS and C8-silane, e.g., adding C8-silane before the addition of TEOS; the hydrothermal treatment condition was adjusted from 70° C. for about one day to 70° C. for about two days, or 70° C. for about one day and 90° C. for the other (about) one day; in order to improve the dispersity of particles in aqueous solution, in particular physiological solution, and reduce the pore blockage caused by TA-silane, the amount of PEG-silane was increased and the amount of TA-silane was reduced, such that the ratio of PEG-silane:TA-silane varied from 2:1 to 7:1; a further example of using PEG-silane alone as the outer surface modification was also conducted.

Along with these adjustments, the MSN particles exhibited good dispersity in PBS and physiological conditions (DLS size of MSNs<60 nm), higher suspension stability (after 37° C. overnight, DLS size of MSNs or DTX@MSNs<60 nm), higher drug loading capacity (the loading efficiency of DTX and CTX is higher than 80% or 70%), and long-term stability of drug-loaded MSN.

Comparison of the dispersity of MSNs in previous research and in the present disclosure:

TABLE 1

| C8-MSN-PEG/TA | TEOS:internal ratio (in mole) modification agent | PEG:TA ratio (in mole) | DLS (d, nm) in medium | |
|---|---|---|---|---|
| | | | H2O | PBS |
| Referenced_MSN (a) | 20:1 (C8-silane) | 2:1 | 31.5 | 40.0 |
| Referenced_MSN (b) | 15:1 (C8-silane) | 2:1 | 29.8 | 76.2 |
| Referenced_MSN (c) | 10:1 (C8-silane) | 2:1 | 39.3 | about 1,000 |
| Referenced_MSN (d) | 20:1 (TMPS) | 2:1 | 36.5 | 43.1 |
| Referenced_MSN (e) | 15:1 (TMPS) | 2:1 | 48.9 | 785.1 |
| Present disclosure (1) | 15:1 (C8-silane) | 2:1 | 45.9 | 45.0 |
| Present disclosure (2) | 15:1 (C8-silane) | 4:1 | 42.9 | 42.2 |
| NTT2_200 (present disclosure) (3)*** | 15:1 (C8-silane) | 7:1 | 44.3 | 43.5 |
| NTT2_200 (present disclosure) (3-1)*** | 15:1 (C8-silane) | 7:1 | 46.4 | 46.5 |
| NTT2_206 (present disclosure) (4) | 10:1 (C8-silane) | 7:1 | 42.7 | 41.5 |
| NTT2_200m (present disclosure) (5) | 15:1 (C8-silane) | ** | 44.5 | 42.1 |
| Present disclosure (6) | 20:1 (TMPS) | 7:1 | 57.8 | 56.6 |
| Present disclosure (7) | 15:1 (TMPS) | 7:1 | 52.8 | 50.9 |

** (only PEG-silane for external surface modification)
***Different batches of NTT2_200 with the same synthetic conditions and reagents According to the data shown in Table 1, it is found that the MSNs optimized for loading the taxane-based chemotherapeutic drugs may exhibit the desired DLS size in PBS even at higher levels of internal surface (pore surface) modification (i.e., lower TEOS:Internal modification agent ratio).

To evaluate the stability under application conditions, the MSNs with C8-silane internal modification and having suitable characteristics were adopted for evaluation. The MSNs were incubated in PBS at 37° C. (as a simulation of human body temperature) overnight and their DLS sizes were measured before and after the incubation. A comparison of the DLS sizes and PDI of DLS sizes of MSNs in previous research and in the present disclosure is shown in Table 2 below.

TABLE 2

| | DLS (d, nm)/PDI in PBS | |
|---|---|---|
| C8-MSN-PEG/TA | Before treatment | After 37° C. overnight |
| Referenced_MSN (a-1)*** | 43.6/0.160 | 55.9/0.206 |
| Referenced_MSN (a-2)*** | 35.1/0.235 | 77.1/0.213 |
| (present disclosure) (1) | 45.0/0.126 | 44.9/0.138 |
| (present disclosure) (2) | 42.2/0.105 | 44.0/0.127 |
| NTT2_200 (present disclosure) (3) | 43.5/0.065 | 44.2/0.084 |

TABLE 2-continued

| C8-MSN-PEG/TA | DLS (d, nm)/PDI in PBS | |
|---|---|---|
| | Before treatment | After 37° C. overnight |
| NTT2_200 (present disclosure) (3-1) | 46.4/0.103 | 46.5/0.103 |
| NTT2_206 (present disclosure) (4) | 41.5/0.176 | 41.8/0.156 |
| NTT2_200m (present disclosure) (5) | 42.1/0.080 | 43.3/0.112 |

***Different batches of referenced MSNs with the synthetic conditions and reagents the same as referenced MSN (a).

Apparently, after incubation at 37° C. in PBS overnight, the DLS sizes of referenced MSNs (a-1) and (a-2) significantly grow and may even exceed 60 nm, while the DLS sizes of the optimized MSNs remain nearly unchanged. The results show that the optimized MSNs remain stable under the simulated application condition. MSNs having internal modification with TMPS were also evaluated.

To further evaluate the applicability after loading the drug under application conditions, the MSNs having suitable characteristics in Table 2 were used for loading with DTX, and the DTX@MSNs were incubated in PBS at 37° C. overnight, with measurement of their DLS sizes. A comparison of the DLS sizes and PDI of DLS sizes of MSNs loaded DTX is shown in Table 3 below:

TABLE 3

| C8-MSN-PEG/TA | DLS (d, nm)/PDI in PBS | |
|---|---|---|
| | Before treatment | After 37° C. overnight |
| DTX@Referenced_MSN (a-3)*** | 31.4/0.209 | 68.4/0.203 |
| DTX@(present disclosure) (1) | 43.2/0.097 | 42.9/0.123 |
| DTX@(present disclosure) (2) | 41.5/0.099 | 42.4/0.111 |
| DTX@NTT2_200 (present disclosure) (3) | 43.6/0.075 | 45.0/0.116 |
| DTX@NTT2_206 (present disclosure) (4) | 38.4/0.086 | 39.7/0.091 |
| DTX@NTT2_200m (present disclosure) (5) | 44.1/0.078 | 45.3/0.121 |

***Different batches of referenced MSNs with the synthetic conditions and reagents the same as referenced MSN (a).

Apparently, after incubation at 37° C. in PBS overnight, the DLS size of referenced DTX@MSNs (a-3) significantly grows larger and even exceeds 60 nm, while the DLS sizes of the inventive DTX@MSNs remain nearly unchanged. The results show that the inventive DTX@MSNs remain stable under the simulated application condition. MSNs having internal modification with TMPS were also evaluated.

Example 2

The MSNs as synthesized in Reference Example 1 with good dispersity and higher suspension stability loaded with DTX or CTX were subject to TEM and DLS measurements, and the results are shown in Table 4 below.

TABLE 4

| | Ave. Size (nm) (TEM) | DLS (d, nm)/ PDI in PBS | Loading Amount | Loading Efficiency |
|---|---|---|---|---|
| DTX@MSN(present disclosure) (1) | 25.1 ± 4.9 | 43.2/0.097 | 3.47% | 64.6% |
| DTX@MSN(present disclosure) (2) | 26.8 ± 3.8 | 41.5/0.099 | 4.37% | 81.4% |
| DTX@NTT2_200 (present disclosure) (3) | 30.2 ± 5.0 | 43.6/0.075 | 4.42% | 94.9% |
| DTX@NTT2_200 (present disclosure) (3-1) | 30.4 ± 4.5 | 47.4/0.076 | 4.56% | 86.8% |
| DTX@NTT2_200m (present disclosure) (5) | 28.1 ± 5.1 | 44.1/0.078 | 7.01% | 81% |
| CTX@NTT2_200 (present disclosure) (3-1) | 30.4 ± 4.5 | 47.2/0.089 | 5.28% | 89.8% |

The loading amount is presented by the weight ratio of the drug to the drug@MSNs. The loading efficiency is presented by the weight ratio of the drug loading to the MSNs to the total amount of drug used for loading. The inventors surprisingly found that the outer surface modification may affect the loading amount and efficiency of the taxane-based chemotherapeutic drugs (DTX and CTX). In particular, the difference among the optimized MSNs (1), (2) and (3) is merely the ratio of the outer surface modification agents, i.e., PEG-silane:TA-silane=2:1, 4:1. 7:1, respectfully. The loading amount (capacity) may increase about 26% to 31% and the loading efficiency may increase about 26% to 47% when the PEG/TA silane ratio becomes larger (i.e., lower level of positively charged modifying agents) in the DTX@MSNs case. MSNs having internal modification with TMPS were also evaluated for loading the taxane-based chemotherapeutic drug(s).

Long-Term (Storage) Stability

The drug loaded MSNs were stored in different media to evaluate the long-term stability via the characteristics shown in Table 5:

TABLE 5

| Stability Factors | Analysis Methods | Attributes |
|---|---|---|
| Integrity and size | TEM | Morphology, particle size and size distribution |
| Suspension/aggregation | DLS | Particle size in $H_2O$ and PBS |
| Drug Loading capacity | HPLC | Drug loading amount |
| Drug substance degradation | HPLC | Total drug amount for the drug integrity in the drug product |
| Leakage of the loaded drug | HPLC | Loading amount and free drug ratio from the drug product |

Testing conditions: NTT2_200 (the optimized MSN (3) in Table 1) was used for loading with DTX and dispersed in each medium at a storage concentration of about 150 mg/mL DTX@NTT2_200 and stored at 4° C. for at least 3 months. TEM size, DLS size (in 2 or PBS) and entrapped DTX of the DTX@NTT2_200 were measured, and the state of solution/dispersion was visually evaluated. The results are summarized below. The stock DTX concentration, i.e., the total DTX concentration in the dispersion (free DTX and DTX@MSNs (entrapped DTX)), was measured as an indicator of degradation of DTX during storage. The entrapped DTX percentage was determined by separating the free DTX from the DTX@MSNs, obtained by centrifuging or filtering a sample amount of dispersion.

TABLE 6

| Storage Medium | TEM size (nm) | DLS size (d · nm)/PDI | Stock DTX conc. (mg/mL) | Entrapped DTX | Solution State |
|---|---|---|---|---|---|
| H₂O (initial) | 26.0 ± 3.1 | 41.9/0.146 (in H₂O) 42.0/0.068 (in PBS) | 6.24 | ~99% | Clear |
| H₂O (3 months) | 26.2 ± 3.0 | 41.6/0.152 (in H₂O) 40.6/0.084 (in PBS) | 6.81⁺⁺ | ~99% | Clear |
| Saline (initial) | 28.5 ± 5.6 | 47.1/0.079 (in H₂O) 48.7/0.081 (in PBS) | 6.52 | ~99% | Clear |
| Saline (3 months) | 27.4 ± 4.9 | 47.0/0.080 (in H₂O) 48.0/0.103 (in PBS) | 6.74⁺⁺ | ~99% | Clear |
| 5% Dextrose (initial) | 29.6 ± 4.3 | 47.0/0.135 (in H₂O) 47.3/0.082 (in PBS) | 6.63 | ~99% | Clear |
| 5% Dextrose (3 months) | 26.5 ± 5.3 | 46.1/0.151 (in H₂O) 47.1/0.084 (in PBS) | 6.66⁺⁺ | ~99% | Clear |
| Citrate buffer (5 mM, pH 6.5) (initial) | 25.9 ± 3.8 | 43.4/0.119 (in H₂O) 43.8/0.111 (in PBS) | 5.77 | ~99% | Clear |
| Citrate buffer (5 mM, pH 6.5) (3 months) | 26.4 ± 3.3 | 42.8/0.109 (in H₂O) 43.3/0.134 (in PBS) | 6.48⁺⁺ | ~99% | Clear |
| Acetate buffer (5 mM, pH 4.5) (initial) | 25.6 ± 3.1 | 43.8/0.140 (in H₂O) 42.3/0.082 (in PBS) | 5.77 | ~99% | Clear |
| Acetate buffer (5 mM, pH 4.5) (3 months) | 27.3 ± 2.7 | 43.4/0.150 (in H₂O) 42.5/0.101 (in PBS) | 6.24⁺⁺ | ~99% | Clear |

⁺⁺The increased stock DTX concentration may have resulted from evaporation of solvent.

According to the results shown above, there were no significant changes in TEM sizes and DLS sizes of DTX@MSNs after 3 months of storage, which may indicate that the MSNs still have intact structure and surface modifications and good dispersity without aggregation in storage media after the long-term storage. In addition, nearly no free DTX in the dispersion was observed and the stock DTX concentration did not decrease after storage, which indicated that the inventive DTX@MSNs exhibit long-term stability in various storage media, at least for the fact that no release and degradation of DTX were observed. MSNs having internal modification with TMPS were also evaluated.

Elemental Analysis and Thermogravimetric Analysis

In the C8-MSN-PEG/TA synthesis process, C8-silane (the aliphatic molecule) was used for modifying the internal surface of pores of MSN, PEG silane (the (i) an organic molecule, oligomer or polymer) and TA silane (the (ii) a positively charged molecule, oligomer or polymer) at different molar ratios were used for the reaction for modulating the PEG/TA ratio on the external surface of MSN. For quantifying the functional group on C8-MSN-PEG/TA nanoparticles, the elemental composition of C8-MSN-PEG/TA particles was measured by an elemental analyzer. The number of C8 group per particle (weight, mg or g) is derived from the mass percent of carbon of C8-MSN (the particle before introducing surface modulating agents), the number of TA group is derived from the mass percent of nitrogen of C8-MSN-PEG/TA particle, and the number of PEG group is derived from the mass percent of carbon thereof, which was obtained by subtracting the mass percent of carbon contributed from the C8 group and the TA group of C8-MSN-PEG/TA from the total mass percent of carbon.

In addition, the total organic group mass percent was measured by thermogravimetric analysis. The total mass percent of C8 group, PEG group, and TA group is derived from the weight loss of C8-MSN-PEG/TA from 150° C. to 800° C. Based on the above analysis and calculation, the numbers of C8 group, TA group, and PEG group of NTT2_200 were about 0.831, 0.094, and 0.425 (mmol/g), respectively, and the total organic mass percent of C8 group, TA group and PEG group of C8-MSN-PEG/TA was about 22.15%.

Example 3

Dose-Related Efficacy of Docetaxel (DTX) and Cabazitaxel (CTX) for TMZ Resistant-Brain Tumors To evaluate the toxicity of DTX and CTX and the efficacy of direct administration of DTX and CTX on treating TMZ resistant brain tumors, 36 mice transplanted with TMZ-resistant brain tumors were used in the experiments, divided into six groups, each group having six mice; details of dosage are noted in Table 7 below:

TABLE 7

| Group Number | Dosage | Median Survival Time (days)* |
|---|---|---|
| 1 (Control) | 20% DMSO + 10% Tween80 in PBS solution or PBS solution | (23)/27 [26.5] |
| 2 (Comparative) | PBS + TMZ (10 mg/kg) | (23)/27 [26.5] |
| 3 | TMZ (10 mg/kg) + 10 mg/kg DTX | (15)/19 |
| 4 | TMZ (10 mg/kg) + 20 mg/kg DTX | (11)/15 |
| 5 | TMZ (10 mg/kg) + 10 mg/kg CTX | (11)/15 |
| 6 | TMZ (10 mg/kg) + 20 mg/kg CTX | (8)/12 |

*(days after 1ˢᵗ injection)/days after implantation of tumor cells

The administration frequency was twice per week until the end of the study. DTX, CTX and PBS were intravenously (IV) injected and TMZ was intraperitoneally (IP) injected into mice. To assess overall survival, mice were monitored up to the point of spontaneous death or approaching moribund status.

Results showed that, in the control and comparative groups (Groups 1 and 2), mice can survive to the end of the testing period ((15)/19, (days after 1ˢᵗ injection)/days after implantation of tumor cells). However, according to the test results of Groups 3 to 6, CTX and DTX would exhibit high toxicity at a dose of 10 mg/kg or above, which is evidenced by a significant decrease of body weight of mice during the testing period and low survival rate of mice (all mice died before the end of the testing period). In addition, mice in Groups 3 to 6 would show discomfort and decreased activity after a few hours of administration of drugs.

To further investigate the toxicity of CTX, the inventors conducted an additional group, Groups 2-1 and 7, details noted in Table 8 below:

TABLE 8

| Group Number | Number of Animals | Dosage |
|---|---|---|
| 2-1 (Comparative) | 4 | TMZ (10 mg/kg) |
| 7 | 5 | TMZ (10 mg/kg) + CTX (5 mg/kg) |

Results showed that, in the comparative Group 2-1, all mice survived 30 days; however, only one mouse in Group 7 survived for over (15)/19, ((days after 1ˢᵗ injection)/days after implantation of tumor cells). The only surviving mouse in Group 7 was continuously administered with drugs at the same dosing frequency to the fifth week; brain and pathological biopsy was conducted on said mice.

Given the above, direct administration of DTX at a dose of 10 mg/kg or higher, or CTX at a dose of 5 mg/kg or higher, may not be used for treating brain cancer due to the high toxicity at the dose level.

Example 4

BBTB Penetration and Tumor-Targeting of the MSN for DTX Delivery

Both BBTB penetration and tumor-targeting capability are basic to and essential for introducing MSN nanoformulation to alter the inefficient therapeutic activity of DTX or CTX itself. In the animal testing model, the orthotopic xenograft brain tumor mice were intravenously injected with fluorescence-labeled MSN (fluorescence-labeled NTT2_200), and the particle distribution in the cerebrovascular of brain tissue region and brain tumor region was acquired by multiphoton fluorescence microscopy. In particular, on the day following the injection, mice brains were collected and fixed for preparing frozen sections. Sections stained with 4',6-diamidino-2-phenylindole (DAPI) (blue signal) were used for visualizing the nucleus to assess brain morphology and identify the tumor tissue, and the distribution of Rhodamine B isothiocyanate (RITC) conjugated MSNs was observed with red signals in fluorescence microscopy. There was an apparent number of MSNs accumulated in the brain tumor region, as compared to normal brain tissues (FIG. 1), which indicated that the MSNs could circulate in blood vessels and accumulate and be retained around the brain tumor site, resulting in higher therapeutic efficacy and lower drug-related toxicity.

Example 5

Figure 2:
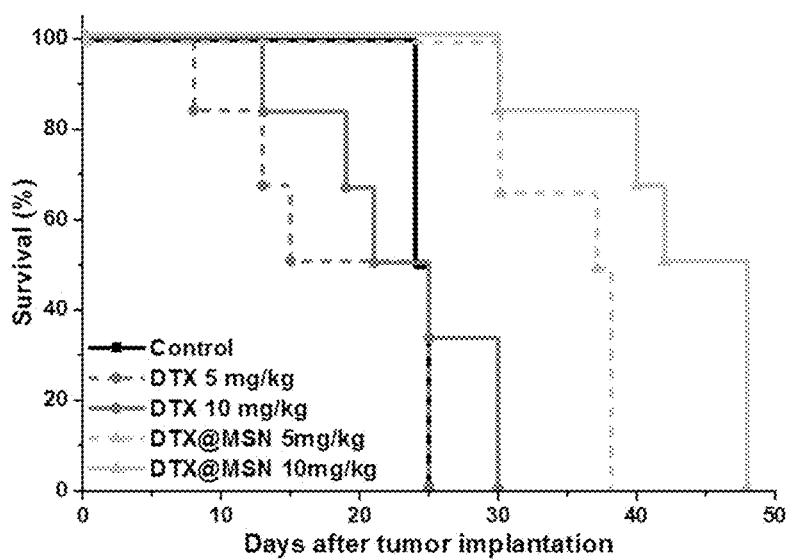
FIG. 2 shows the experimental details and results of DTX and DTX@MSN in the orthotopic TMZ-resistant brain tumor mouse model.
Figure 2:
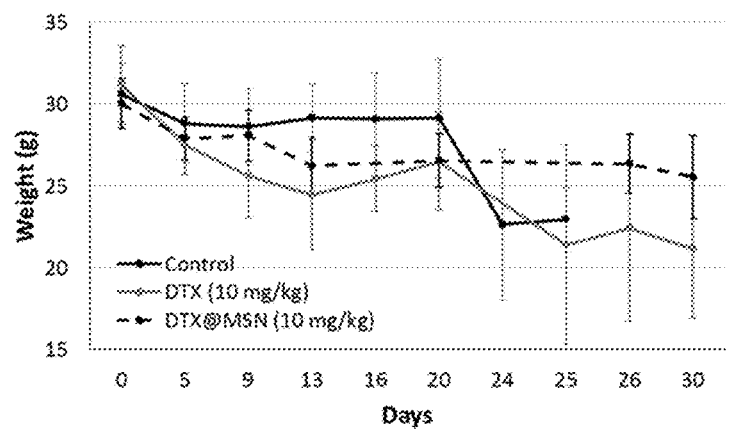

Dose-Related Efficacy of Docetaxel (DTX) and DTX@MSN for TMZ Resistant-Brain Tumors As noted above, the resistance to TMZ often becomes the limiting factor for effective treatment. Given this, the TMZ-resistant orthotopic xenograft GBM model is a good model to verify the effectiveness of therapeutics. Orthotopic TMZ-resistant brain tumor mice were intravenously injected with DTX alone and DTX in nanoformulation (DTX@MSN, the type of MSN was NTT2_200) on days 5, 9, 13, 26, 30, and 34. Body weight and survival time of animals were monitored up to the point of spontaneous death. DTX@MSN exhibited effective tumor inhibition and significantly longer overall survival as compared to the control and DTX alone treatment group. The percentage of increase in life span of high dose DTX@MSN group was about 83.7% improvement compared to control, and the survival improvement of DTX@MSN was dose-related. By contrast, the median survival time of the DTX alone group was similar to or shorter than the control group because of less efficacy and higher toxicity of DTX alone, which was the same as observed in the clinic. Furthermore, the mice treated with DTX alone presented immobility, interaction deficits, and more body weight loss than the DTX@MSN due to the toxicity (FIG. 2).

Figure 3:
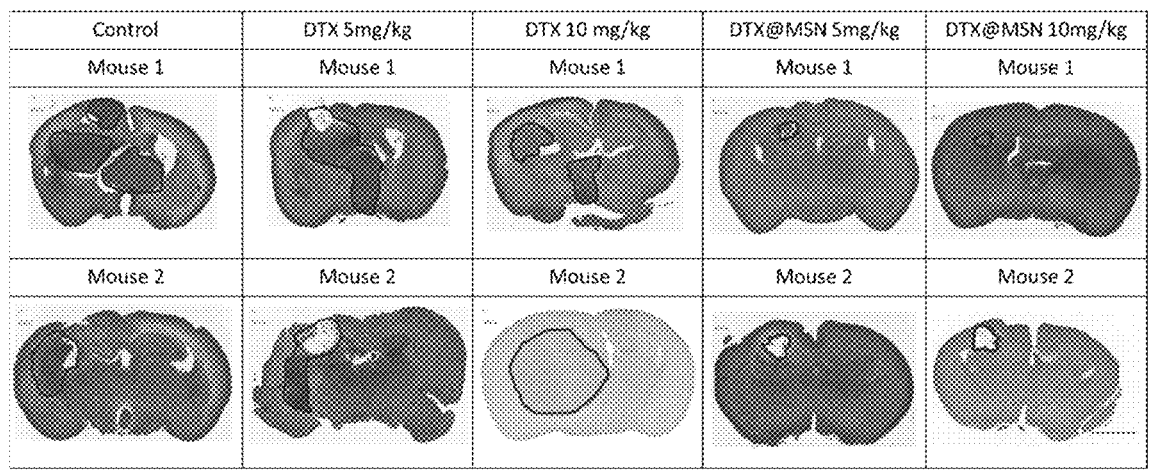
FIG. 3 shows the H&E stain of brain tissues of mice injected with PBS (control), DTX (5 mg/kg and 10 mg/kg), and DTX@MSN (5 mg/kg and 10 mg/kg), respectively.

Histological micrographs of tissue sections in brain tumors were also acquired to assess the tumor size after treatment (see, FIG. 3). The tumor size of DTX@MSN treated groups, either 5 mg/kg or 10 mg/kg dose levels, were significantly smaller than DTX alone treated group and control. In contrast, the tumor size of DTX alone treated groups was similar to the control group indicating that DTX alone was ineffective against brain tumor growth (FIG. 3). In addition, the expression levels of apoptosis biomarkers (caspase 3 and cleaved PARP apoptosis markers are related to DTX-induced cancer cell death) in brain tissues were positively correlated with the anti-tumor efficacy of DTX@MSN and DTX alone, which demonstrated that DTX was delivered by MSN into brain tumor and induce cancer cell death.

Example 6

Dose-Related Efficacy of Docetaxel@MSN (DTX@MSN) in Combination with TMZ for TMZ Resistant-Brain Tumors To evaluate the toxicity of DTX and the efficacy of direct administration of DTX loaded in the mesoporous silica nanoparticles (NTT2_200 shown in Example 1) of the disclosure on treating TMZ resistant brain tumors, orthotopic TMZ-resistant brain tumor mice were used in the experiments with one group having four mice (Control) and the other groups each having six mice. Since the inventors recognized that the dose level at 10 mg/kg or higher may exhibit high toxicity, the dose level in this experiment was adjusted. Details of dosage and mean survival time are noted in Table 9 below:

TABLE 9

| Group Number | Dosage | Median Survival Time (days)* |
|---|---|---|
| 1 (Control) | 20% DMSO + 10% Tween80 in PBS solution or PBS solution | 27 [26.5] |
| 2 (Comparative) | PBS + TMZ (10 mg/kg) | 27 [26.5] |
| 8 | TMZ (10 mg/kg) + 5 mg/kg DTX@MSN Six doses in total | 43 |
| 9 | TMZ (10 mg/kg) + 10 mg/kg DTX@MSN Five doses in total | 41 [40.5] |

*days after implantation of tumor cells

Figure 4:
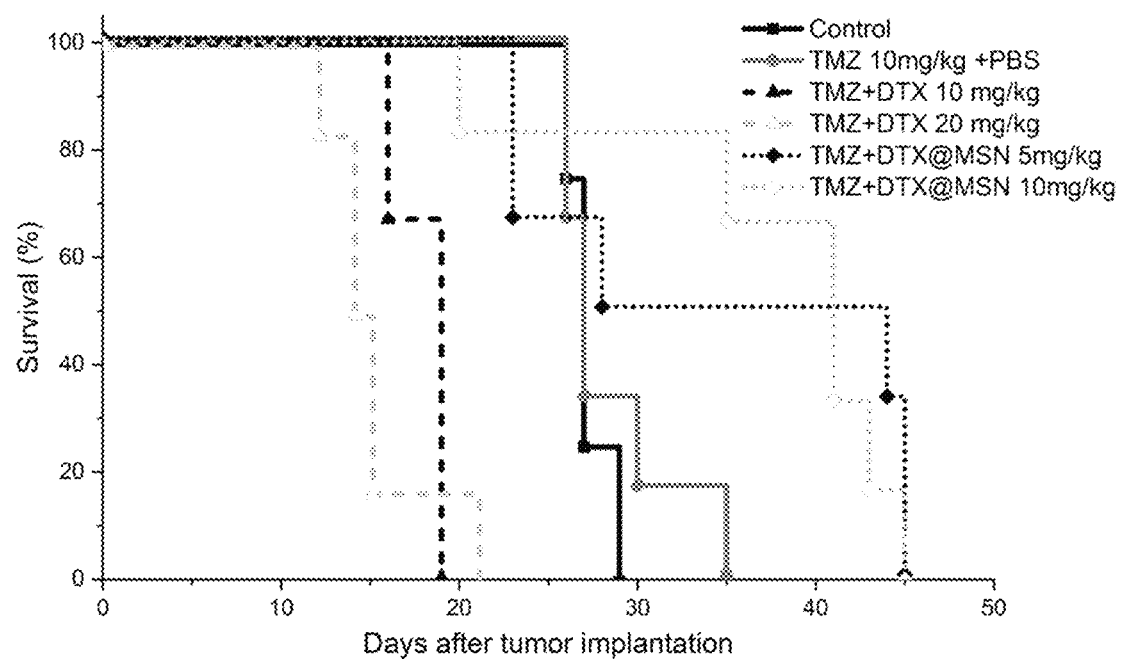
FIG. 4 shows the experimental details and results of using DTX or DTX@MSNs in combination with TMZ for treating mice in the orthotopic TMZ-resistant brain tumor mouse mode.

It is observed that mice in Groups 8 and 9 did not exhibit lower activity or other unusual conditions, during the administration period, only decrease in body weight. The median survival time (the time at which fractional survival is equal to 50%) in Groups 8 and 9 was significantly longer than that in Groups 1 and 2. In particular, mice treated with TMZ alone (Group 2) had a similar survival time to the control group (Group 1), demonstrating that the tumor cells were resistant to TMZ. DTX in MSN nanoformulation (DTX@MSN) in combination with TMZ significantly increased the overall survival over the control groups (PBS and TMZ) and the DTX in combination with TMZ group (FIG. 4). It should be noted that the higher toxicity of TMZ plus DTX may limit the efficacy and lead to immobility, interaction deficits, significant body weight loss, and premature death of the treated mice, and thus should be carefully applied.

All the results indicate that MSN nanoformulation, either used alone or in combination with TMZ, can deliver DTX across BBTB to target brain tumors, resulting in DTX@MSN efficiently inhibiting proliferation and inducing apoptosis of cancer cells, diminishing drug-related toxicities, and significantly increasing overall survival, thus offering superior effects over DTX alone in treating brain cancers or cancers that have metastasized into the brain.

Example 7

Dose-Related Efficacy of Cabazitaxel@MSN (CTX@MSN) in Combination with TMZ for TMZ Resistant-Brain Tumors To evaluate the toxicity of CTX in combination with TMZ and the efficacy of intravenous administration of CTX loaded in the mesoporous silica nanoparticles of the disclosure (here, NTT2_200 shown in Example 1) in combination with TMZ on treating TMZ resistant brain tumors, orthotopic TMZ-resistant brain tumor mice were used in experiments with one group having four mice (Control) and the other groups each having six mice. Since the inventors recognized that the dose level at 10 mg/kg or higher may exhibit high toxicity, the dose level in this experiment was adjusted. Details of dosage and mean survival time are

TABLE 10

| Group Number | Dosage | Median Survival Time (days)* |
|---|---|---|
| 1 (Control) | 20% DMSO + 10% Tween80 in PBS solution or PBS solution | 27 [26.5] |
| 2 (Comparative) | PBS + TMZ (10 mg/kg) | 27 [26.5] |
| 10 | TMZ (10 mg/kg) + 5 mg/kg CTX@MSN Six doses in total | 40 |
| 11 | TMZ (10 mg/kg) + 10 mg/kg CTX@MSN Five doses in total | 19 |

*days after implantation of tumor cells

Figure 5:
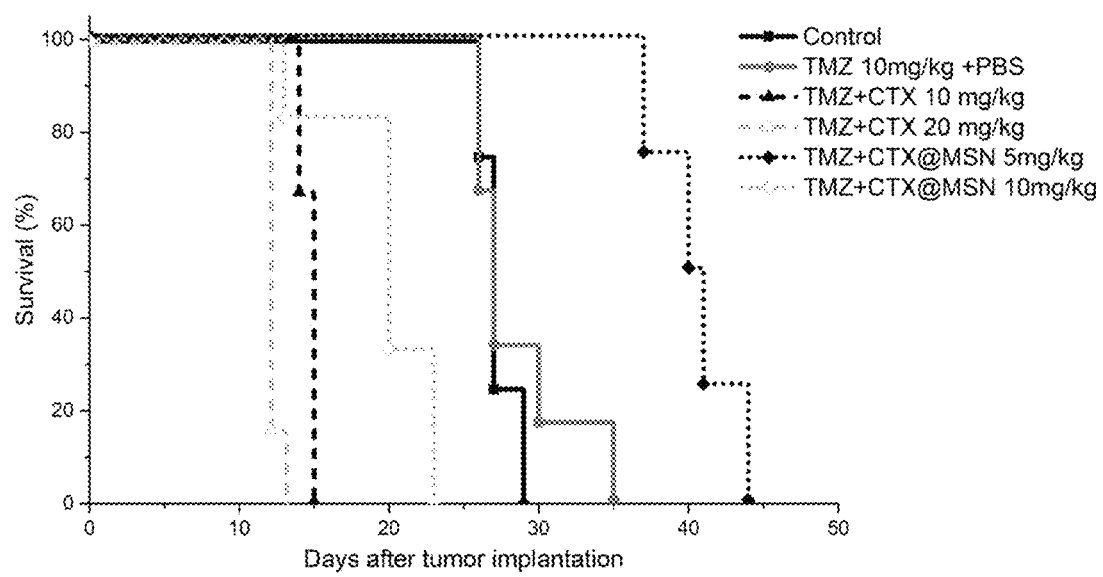
FIG. 5 shows the experimental details and results of using CTX or CTX@MSNs in combination with TMZ for treating mice in the orthotopic TMZ-resistant brain tumor mouse mode.

CTX in combination with TMZ exhibited high toxicity at a dose of 10 mg/kg, which is evidenced by a significant decrease in body weight and premature death of mice during the testing period. Although CTX@MSN in combination with TMZ reduced the toxicity, resulting in a longer survival time than the CTX group, the 10 mg/kg was still too high to tolerate for the mice. Reducing the dose level of CTX@MSN to 5 mg/kg, the tolerant dose for mice, resulted in the exhibition of CTX@MSN in combination with TMZ efficacy and prolongation of survival time (see, FIG. 5).

Biopsies of brains of mice in Groups 1 to 3, 5 and 8 to 11 (not shown) were also conducted for evaluating the treatment efficacy on brain cancers. Brains were retrieved after the mice naturally died and then were stained via hematoxylin and eosin stain (H&E stain). For mice in Groups 1 and 2, it could be observed that the tumors significantly grew. For mice in Groups 3 and 5, though mice died before the testing period ended, the tumor size was smaller than in Groups 1 and 2. On the other hand, the data for mice in Groups 8 to 11 were promising. In particular, the tumor size of mice in Groups 8 to 11 was significantly smaller than that of mice in Groups 1 or 2, and the tumor of mice in Group 11 even nearly disappeared (though mice in said group died earlier). In addition, the shrinkage of tumors is dose-dependent, since the tumor size of mice in Group 9 (TMZ (10 mg/kg)+10 mg/kg DTX@MSN) and in Group 11 (TMZ (10 mg/kg)+10 mg/kg CTX@MSN) was smaller than that in Group 8 (TMZ (10 mg/kg)+5 mg/kg DTX@MSN) and in Group 10 (TMZ (10 mg/kg)+5 mg/kg CTX@MSN), respectively. In addition, the therapeutic effect of CTX@MSN may be superior to that of DTX@MSN.

Example 8

Phase I/II Study of Docetaxel in MSN Nanoformulation in Adults with Recurrent or Refractory High-grade Gliomas and Solid Tumors with and without Brain Metastasis Indications As treatment of recurrent or refractory high-grade gliomas and advanced solid tumors with or without brain metastases.

Study Objectives

Phase I/II, multicenter, open-label trial to evaluate the safety, tolerability, PK and efficacy of DTX or CTX in MSN nanoformulation as a monotherapy or combined therapy in high-grade glioma and advanced solid tumors with or without brain metastases.

Study Design

The study consists of three phases: phase Ia (dose escalation with monotherapy), phase Ib (dose escalation with and Temozolomide (TMZ) combination therapy) in high-grade glioma. In phase II, the maximum tolerated dose of nanoformulation recommended from phase Ia are examined in solid tumor with and without brain metastasis.

Treatment Duration and End of Study

Phase Ia

Nanoformulation are tested in acceleration iteration dose escalation manner. All patients will be given intravenous administration of nanoformulations on day 1 of 14-day or 21-day cycles, on day 1 and day 22 of 28-day or 42-day cycles until disease progression, toxicity, withdrawal of consent, or termination of the study.

Phase Ib

The combination of nanoformulations with TMZ are tested in 3+3, 3+4, 4+3 or 4+4 dose escalation design.

Dosing: administration of nanoformulations on day 1 of 14-day or 21-day cycles, or on day 1 and day 22 of 28-day or 42-day cycles; administration of TMZ: 75 ng/m2 for 42 days concomitant with focal radiotherapy followed by initial maintenance dose of 150 mg/m2 once daily for Days 1-5 of a 28-day cycle of TMZ for 6 cycles.

End of study: until disease progression, toxicity, withdrawal of consent, or termination of the study.

Phase II

The maximum tolerant dose (MTD) recommended from phase Ia in multiple expansion cohort of each cancer type of study. Monotherapy with nanoformulations are tested in fixed dose on HGGs, mBC, mNSCL, and mCRPC to determine clinical efficacy.

Timing of dosing: on day 1 of 14-day or 21-day cycles, or on day 1 and day 22 of 28-day or 42-day cycles.

Duration: infusion 1 hr, 14 days or 21 days per cycle.

End of study: until disease progression, toxicity, withdrawal of consent, or termination of the study Study Endpoints Phase Ia and Ib endpoints: tolerability, safety, pharmacokinetic.

Phase II:

Primary endpoints: PFS, OS

Secondary endpoints: Quality of life

Study Treatment

Phase Ia:

Study drug: DTX in MSN nanoformulation or CTX in MSN nanoformulation

Dose levels: 4 dose levels

One treatment cycle: All patients are given intravenous administration of nanoformulations on day 1 of 14-day or 21-day cycles, or on day 1 and day 22 of 28-day or 42-day cycles.

Subjects may continue treatment until disease progression, toxicity, withdrawal of consent, or termination of the study.

Phase Ib:

Study drug: Combination of DTX in nanoformulation with TMZ or CTX in nanoformulation with TMZ Dose levels: 2 dose levels One treatment cycle: All patients are given intravenous administration of nanoformulation on day 1 of 14-day or 21-day cycles, or on day 1 and day 22 of 28-day or 42-day cycles; administration of TMZ: 75 mg/m2 for 42 days concomitant with focal radiotherapy followed by initial maintenance dose of 150 mg/m2 once daily for days 1-5 of a 28-day cycle of TMZ for 6 cycles.

Subjects may continue treatment until disease progression, toxicity, withdrawal of consent, or termination of the study.

Phase II:

Study drug: DTX in MSN nanoformulation or CTX in MSN nanoformulation

Dose level: The maximum tolerant dose (MTD) recommended from phase Ia

One treatment cycle: on day 1 of 14-day or 21-day cycles, or on day 1 and day 22 of 28-day or 42-day cycles.

Control drug: None, use 14 or 21 days/cycle, 2 treatment cycle, real world data.

In summary, the claimed taxane-based chemotherapeutic drug@MSNs (e.g., CTX@MSN and DTX@MSN) may provide superior effect over existing drugs in treating brain tumors and metastatic brain cancer, in particular drug-resistant brain tumor, with longer survival time and fewer side effects such as decreased activity, injection site reactions (pain, redness, or swelling), nausea, vomiting, diarrhea, muscle pain, joint pain, burning, tingling, numbness, pain in the hands, arms, feet, or legs, etc.

The ingredients, reaction conditions and parameters illustrated in the examples are merely for illustrative purposes and are not intended to limit the material or the preparation method.

A person of ordinary skill in the art of the subject invention should understand that variations and modification may be made to the teaching and the disclosure of the subject invention without departing from the spirit and scope of the subject application. Based on the contents above, the subject application intends to cover any variations and modifications thereof with the proviso that the variations or modifications fall within the scope as defined in the appended claims or their equivalents.

We claim:

1. A method of treating a brain cancer or brain metastasis in a subject, comprising intravenously administering to the subject a mesoporous silica nanoparticle loaded with a taxane-based chemotherapeutic drug within its pores, wherein:
    the taxane-based chemotherapeutic drug is selected from the group consisting of cabazitaxel (CTX) and docetaxel (DTX), and
    the mesoporous silica nanoparticle has the following characteristics:
    (a) surface modification with (i) an organic molecule, oligomer or polymer and (ii) a positively charged molecule, oligomer or polymer, wherein the molar ratio of (i) and (ii) ranges from 60:1 to 4:1; and
    (b) pore internal surface modification with a terminal hydrocarbyl moiety.

2. The method according to claim 1, wherein the taxane-based chemotherapeutic drug is DTX.

3. The method according to claim 1, wherein the mesoporous silica nanoparticle further has at least one of the following characteristics:
    (a') surface modification with (i) an organic molecule, oligomer or polymer and (ii) a positively charged molecule, oligomer or polymer, wherein the molar ratio of (i) and (ii) ranges from 10:1 to 5:1;
    (b') pore internal surface modification with a terminal hydrocarbyl moiety derived from long-chain alkyl silanes with 4 to 18 carbon atoms;
    (c) an average particle size of 60 nm or less, measured by TEM;
    (d) an average dynamic light scattering particle size of 60 nm or less, measured in phosphate buffered saline (PBS) by dynamic light scattering; and
    (e) surface modification with (i) an organic molecule, oligomer or polymer.

4. The method according to claim 3, wherein the mesoporous silica nanoparticle further has characteristics of (a') and (b'), characteristics of (e) and (b), or characteristics of (b) and (d).

5. The method according to claim 3, wherein the mesoporous silica nanoparticle further has characteristics of (a'), (b'), (c) and (d), or further has characteristics of (e), (b'), (c) and (d).

6. The method according to claim 1, wherein the brain cancer is resistant to a drug selected from the group consisting of temozolomide (TMZ), bevacuzumab, belzutifan, carmustine, everolimus, lomustine and naxitamab-gqgk.

7. The method according to claim 1, wherein (1) the organic molecule, oligomer or polymer (i) is selected from poly(ethylene glycol) (PEG), poly(propylene glycol) (PPG), PEG-PPG copolymers, and combinations thereof, (2) the positively charged molecule, oligomer or polymer (ii) is selected from (N-[3-(trimethoxysilyl) propyl]-N,N,N-trimethylammonium chloride), N-[3-(Trimethoxysilyl)propyl] ethylenediamine, polyethylenimine (PEI); alkoxylsilane-terminated (poly)alkylene (poly)amine, organo-alkoxysilane with amino group(s), and combinations thereof, or (3) both (1) and (2).

8. The method according to claim 1, wherein the pore internal surface modification is achieved by using a silane(s) having no terminal hydrocarbyl moiety and a silane(s) having at least one terminal hydrocarbyl moiety and the molar ratio of the silane(s) having no terminal hydrocarbyl moiety to the silane(s) having at least one terminal hydrocarbyl moiety, is less than 50:1.

9. The method according to claim 1, wherein the terminal hydrocarbyl moiety is selected from the group consisting of a terminal aromatic moiety, a terminal aliphatic moiety, a terminal cycloaliphatic moiety, and combinations thereof.

10. The method according to claim 1, further comprising administration of an additional active agent.

* * * * *